United States Patent [19]
Doscher et al.

[11] Patent Number: 5,455,263
[45] Date of Patent: Oct. 3, 1995

[54] METHODS FOR THE CONTROL AND THE PROTECTION OF WARM-BLOODED ANIMALS AGAINST INFESTATION AND INFECTION BY HELMINTHS, ACARIDS AND ARTHROPOD ENDO- AND ECTOPARASITES

[75] Inventors: Mary E. Doscher, Trenton; Dale G. Brown, Hopewell, both of N.J.; Robert E. Diehl, Yardley, Pa.; Donald P. Wright, Jr., Hopewell Township, N.J.

[73] Assignee: American Cyanamid Company, Wayne, N.J.

[21] Appl. No.: 90,864

[22] Filed: Jul. 13, 1993

Related U.S. Application Data

[63] Continuation of Ser. No. 395,828, Aug. 18, 1989, abandoned, which is a continuation-in-part of Ser. No. 208,841, Jun. 23, 1988, Pat. No. 5,010,098, which is a continuation-in-part of Ser. No. 79,545, Jul. 29, 1987, abandoned.

[51] Int. Cl.$^6$ ..................................................... A01N 43/36
[52] U.S. Cl. .......................... 514/422; 514/423; 514/424; 514/427
[58] Field of Search ..................................... 514/422, 423, 514/424, 427

[56] References Cited

U.S. PATENT DOCUMENTS

| | | | |
|---|---|---|---|
| 3,428,648 | 2/1969 | Umio et al. | 514/427 |
| 3,963,746 | 6/1976 | Bailey et al. | 548/540 |
| 4,495,358 | 1/1985 | Koyama et al. | 548/550 |
| 4,705,801 | 11/1987 | Martin et al. | 514/423 |
| 4,904,687 | 2/1990 | Wollweber et al. | 548/561 |
| 4,929,634 | 5/1990 | Herman et al. | 514/422 |

OTHER PUBLICATIONS

Chemical Abstracts (111 194576w) 1989.

*Primary Examiner*—Marianne M. Cintins
*Assistant Examiner*—Kevin E. Weddington
*Attorney, Agent, or Firm*—John W. Hogan, Jr.

[57] ABSTRACT

This invention relates to methods controlling, and protecting warm-blooded animals from infestation and infection by helminths, acarids and arthropod endo- and ectoparasites by administering or applying to the animals a substituted arylpyrrole compound.

7 Claims, No Drawings

METHODS FOR THE CONTROL AND THE PROTECTION OF WARM-BLOODED ANIMALS AGAINST INFESTATION AND INFECTION BY HELMINTHS, ACARIDS AND ARTHROPOD ENDO- AND ECTOPARASITES

This application is a continuation of U.S. Ser. No. 07/395,828, filed Aug. 18, 1989, now abandoned which is a continuation-in-part of U.S. Ser. No. 07/208,841 filed Jun. 23, 1988, now U.S. Pat. No. 5,010,098 which is a continuation-in-part of U.S. Ser. No. 07/079,545 filed Jul. 29, 1987, now abandoned.

BACKGROUND OF THE INVENTION

It is an object of this invention to provide novel arylpyrrole compounds and a method for treating, controlling, preventing and protecting warm-blooded animals from infestation and infection by helminths, acarids and arthropod endo and ectoparasites by administering thereto a substituted arylpyrrole compound. It is also an object of this invention to provide a method for protecting meat-producing and companion animals from infestation by arthropod endo and ectoparasites by applying to said animals a substituted arylpyrrole compound.

These and other objects will become more apparent from the detailed description of the invention set forth below.

SUMMARY OF THE INVENTION

The present invention relates to novel arylpyrrole compounds and to methods and compositions for treating, controlling, preventing and protecting warm-blooded animals against infestation and infection by helminths, acarids and arthropod endo- and ectoparasites, by orally or parenterally administering to said animals or topically applying to said animals, an anthelmintically, acaricidally or parasiticidally effective amount of a substituted arylpyrrole compound.

DESCRIPTION OF THE PREFERRED EMBODIMENTS

The present invention is also directed to methods for preparing the arylpyrrole compounds. The novel arylpyrrole compounds of the present invention have the structural formula illustrated as formula I:

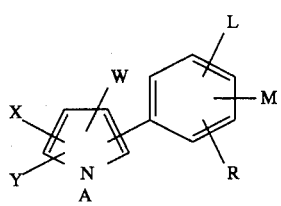

wherein X is F, Cl, Br, I, or $CF_3$; Y is F, Cl, Br, I, $CF_3$ or CN; W is CN or $NO_2$ and A is H; $C_1$–$C_4$ alkyl optionally substituted with from one to three halogen atoms, one hydroxy, one $C_1$–$C_4$ alkoxy or one $C_1$–$C_4$ alkylthio, one phenyl optionally substituted with $C_1$–$C_3$ alkyl or $C_1$–$C_3$ alkoxy or with one to three halogen atoms, one phenoxy optionally substituted with one to three halogen atoms or one benzyloxy optionally substituted with one halogen substituent; $C_1$–$C_4$ carbalkoxymethyl; $C_3$–$C_4$ alkenyl optionally substituted with from one to three halogen atoms; cyano; $C_3$–$C_4$ alkynyl optionally substituted with one halogen atom; di-($C_1$–$C_4$ alkyl) aminocarbonyl; or $C_4$–$C_6$ cycloalkylaminocarbonyl; L is H, F, Cl or Br; and M and R are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$, $R_1CF_2Z$, $R_2CO$ or $NR_3R_4$, and when M and R are on adjacent positions and taken with the carbon atoms to which they are attached they may form a ring in which MR represents the structure:

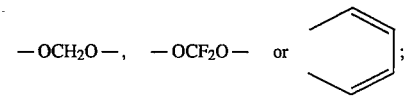

Z is $S(O)n$ or O; $R_1$ is H, F, $CHF_2$, CHFCl, or $CF_3$; $R_2$ is $C_1$–$C_3$ alkyl, $C_1$–$C_3$ alkoxy, or $NR_3R_4$; $R_3$ is H or $C_1$–$C_3$ alkyl; $R_4$ is H, $C_1$–$C_3$ alkyl, or $R_5CO$; $R_5$ is H or $C_1$–$C_3$ alkyl; and n is an integer of 0, 1 or 2.

The term $C_4$–$C_6$ cycloalkylamino carbonyl means a $C_4$ to $C_6$ cycloalkylamino group attached directly to the carbonyl group through the nitrogen atom.

A substituted arylpyrrole compound suitable for the present invention has the following structure:

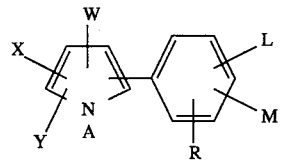

wherein X is H, F, Cl, Br, I or $CF_3$; Y is H, F, Cl, Br, I, $CF_3$ or CN; W is CN or $NO_2$ and A is H; $C_1$–$C_4$ alkyl optionally substituted with from one to three halogen atoms, one hydroxy, one $C_1$–$C_4$ alkoxy or one $C_1$–$C_4$ alkylthio, one phenyl optionally substituted with $C_1$–$C_3$ alkyl or $C_1$–$C_3$ alkoxy with one to three halogen atoms, one phenoxy optionally substituted with one to three halogen atoms or one benzyloxy optionally substituted with one halogen substituent; $C_1$–$C_4$ carbalkoxymethyl; $C_3$–$C_4$ alkenyl optionally substituted with one to three halogen atoms; cyano; $C_3$–$C_4$ alkynyl optionally substituted with one halogen atom; di-($C_1$–$C_4$ alkyl) aminocarbonyl; or $C_4$–$C_6$ cycloalkylaminocarbonyl; L is H, F, Cl or Br; and M and R are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$, $R1CF_2Z$, $R_2CO$ or $NR_3R_4$, and when M and R are on adjacent positions and taken with the carbon atoms to which they are attached they may form a ring in which MR represents the structure:

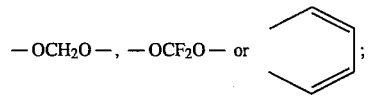

Z is $S(O)n$ or O; $R_1$ is H, F, $CHF_2$, CHFCl, or $CF_3$; $R_2$ is $C_1$–$C_3$ alkyl, $C_1$–$C_3$ alkoxy, or $NR_3R_4$; $R_3$ is H or $C_1$–$C_3$ alkyl; $R_4$ is H, $C_1$–$C_3$ alkyl, or $R_5CO$; $R_5$ is H or $C_1$–$C_3$ alkyl; and n is an integer of 0, 1 or 2.

In practice, the substituted arylpyrrole may be orally administered to the animals in the form of a paste, capsule, pill, bolus, tablet, drench or the like, containing sufficient formula I arylpyrrole to provide the treated animal with about 0.2 mg/kg to 200 mg/kg of animal body weight and preferably 0.5 mg/kg to 100 mg/kg of animal body weight of said arylpyrrole.

The arylpyrrole may also be administered to the animals in or with their feed or drinking water. In one embodiment of the invention an arylpyrrole selected from 3-bromo-5-(p-chlorophenyl)pyrrole-2,4-dicarbonitrile; 4-bromo-2-(p-chlorophenyl)-1-(ethoxymethyl)- 5-(trifluoromethyl)pyrrole-3-carbonitrile; 4-bromo-2-(3,4-dichlorophenyl)-1-(ethoxymethyl)- 5-(trifluoromethyl)-pyrrole-3-carbonitrile; 4-5-dichloro-1-(hydroxymethyl)- 2-($\alpha,\alpha,\alpha$-trifluoro-p-tolyl)pyrrole-3-carbonitrile acetate ester; and 3-nitro-2-phenyl-4,5-bis(trifluoromethyl)pyrrole is generally dispersed in the feed or drinking water in sufficient amount to provide about 0.1 ppm to 500 ppm and preferably 0.5 ppm to 100 ppm of the arylpyrrole or it may be applied as a top dressing for the daily ration. For dispersion in the drinking water, the pyrrole may first be dissolved in a pharmaceutically acceptable water miscible solvent such as ethanol and then dispersed in the water. Similarly for use in the feed the arylpyrrole may be dispersed in a suitable solvent such as acetone and sprayed on the feed and blended therewith or it may be prepared as an animal feed premix or concentrate and blended with the feed prior to use.

For parenteral administration the arylpyrrole may be dispersed in a physiologically acceptable solvent, for subcutaneous or intramuscular injection or it may be dispersed in a fat or wax or mixture thereof containing surfactant, preservative, stabilizer, salt, buffer and oil for this method of treatment or for administration as an implant. Vehicle components useful in these preparations include glyceryl dioleate, saline, capric/caprylic triglycerides, soya oil, diethyl succinate, aluminum monostearate gel and carbowax.

As indicated above, the arylpyrroles suitable for this invention may also be applied topically to meat producing and companion animals to control, prevent or treat said animals against infestation by arthropod ectoparasites and acarids. The active compounds can be prepared as aqueous dips for swine, cattle, sheep, horses, goats, poultry, dogs, cats and the like or they may be prepared as wettable powders, emulsifiable concentrates, aqueous flowables and the like, which are dispersed in water and applied as aqueous sprays to the fur or hide of the animals. Such sprays usually contain about 0.1 ppm to 5000 ppm and preferably 0.5 ppm to 1000 ppm of the active formula I arylpyrrole.

Advantageously, the arylpyrroles may also be prepared as pour-on formulations and poured on the backs of the animals such as swine, cattle, sheep, horses, goats, poultry and companion animals to protect them against infestation by acarids and arthropod ectoparasites. Such pour-on compositions are generally prepared by, dissolving, suspending or emulsifying the arylpyrrole in a suitable nontoxic pharmacologically acceptable diluent for pour-on administration. The diluent must be compatible with the arylpyrrole and should not be a source of irritation or damage to the animals skin or hair. Such diluents include mono and polyhydric alcohols, vegetable oils, spreading oils, aliphatic and aromatic hydrocarbons, lower alkyl ketones, esters and fatty acids.

A typical pour-on formulation includes about 0.5% to 30% by weight of the substituted arylpyrrole, about 0.5 to 30% by weight of a spreading oil, about 30% to 60% by weight of an aliphatic or aromatic hydrocarbon, mono or polyhydric, alcohol lower alkyl ketone or mixtures thereof and 0 to about 20% by weight of a vegetable or mineral oil. Another typical pour-on contains about 45% by weight of xylene, about 25% by weight of cyclohexanone, about 15% by weight of arylpyrrole, about 10% by weight of corn oil or mineral oil and about 5% by weight of other pharmacologically acceptable diluents such as surfactants, spreading agent, antifoam agents or the like. Among the spreading oils that can be utilized in pour-on formulations of this invention are fatty acids, fatty acid esters, triglycerides and fatty alcohols including isopropyl myristate, capryl/caproic acid esters of saturated ($C_{12}$–$C_{18}$) fatty alcohols with waxy fatty acid esters and isopropyl palmitate. Alcohols, glycols and ketones useful in the present invention include ethyl alcohol, isopropyl alcohol, propylene glycol, dipropylene glycol, benzyl alcohol, dipropylene glycol monoethyl ether, cyclohexanone, methylethyl ketone, methylisobutyl ketone and N-butoxybutylethoxyethanol. Vegetable oils that may be suitable for the present invention are corn oil, olive oil, peanut oil, sunflower oil, cotton-seed oil and soybean oil. Hydrocarbons useful in the present invention include xylene and toluene. Surfactants may also be utilized in the formulations if desired.

A preferred group of novel arylpyrroles of the present invention are illustrated by formula II:

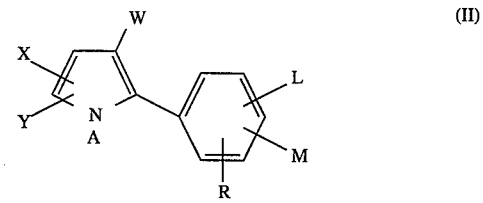

wherein A, L, M, R, W, X and Y are as described above.

Another preferred group of novel arylpyrroles of this invention are represented by formula III:

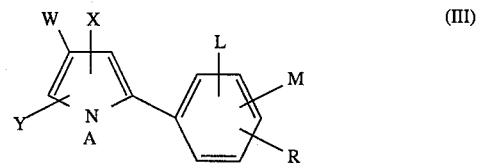

wherein A, L, M, R, W, X and Y are as described above.

Another group of preferred arylpyrroles of the invention are depicted by formula IV:

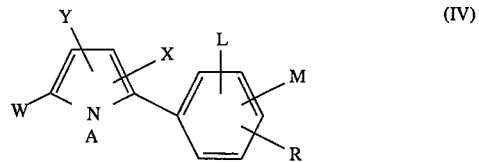

wherein A, L, M, R, W, X and Y are as described above.

Yet another group of preferred arylpyrroles of this invention are delineated by formula V:

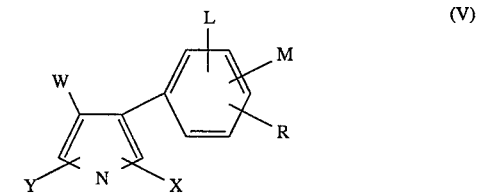

wherein A, L, M, R, W, X and Y are as described above; and still other preferred arylpyrroles of the invention as depicted by formulas VI and VII:

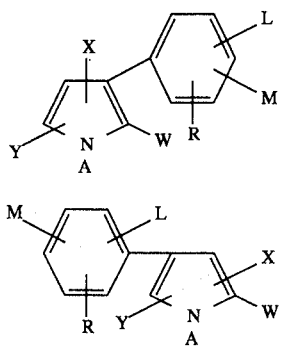

wherein A, L, M, R, W, X and Y are described above.

Preferred formula I arylpyrroles of the invention are those in which A is hydrogen or $C_1$–$C_4$ alkoxymethyl; W is CN or $NO_2$; L is hydrogen or F; X and Y are each Cl, Br or $CF_3$; M is H, F, Cl or Br; and R is F, Cl, Br, $CF_3$ or $OCF_3$.

The substituted arylpyrrole compounds of the invention having the structure of formula I, wherein A is hydrogen; W is CN and X, Y, L, M and R are as described above, can be prepared by reacting N-formyl-phenyl-DL-glycine or a substituted N-formylphenylycine represented by the structure formula VIII:

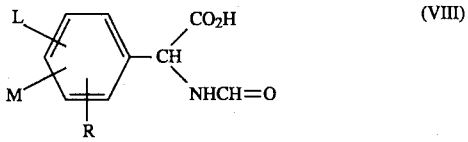

wherein L is H, F, Cl or Br; R and M are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$, $R1CF_2Z$, $R_2CO$ or $NR_3R_4$ and when on adjacent positions and taken together with the carbon atoms to which they are attached, M and R may form a ring in which MR represents the structure:

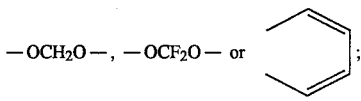

Z is S(O)n or O; $R_1$ is H, F, $CHF_2$, CHFCl or $CF_3$; $R_2$ is $C_1$–$C_3$ alkyl, $C_1$–$C_3$ alkoxy or $NR_3R_4$; $R_3$ is H or $C_1$–$C_3$ alkyl; $R_4$ is H, $C_1$–$C_3$ alkyl or $R_5CO$; $R_5$ is H or $C_1$–$C_3$ alkyl and n is an integer of 0, 1 or 2; with at least an equivalent amount of a 2-chloroacrylonitrile and two to three equivalents of acetic anhydride. The reaction is conducted at an elevated temperature, preferably about 70° to 100° C.

The reaction can be illustrated as follows:

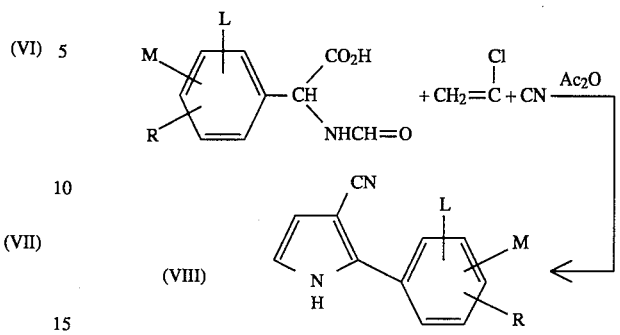

Conversion of the thus prepared 2-phenylpyrrole-3-carbonitrile or 2-(substituted phenyl)pyrrole-3-carbonitrile to the corresponding formula II, 4-halo, 5-halo or 4,5-dihalo-2-(substituted phenyl)pyrrole-3-carbonitrile, is readily achieved by reaction of the above said 2-phenylpyrrole-3-carbonitrile or 2-(substituted phenyl)pyrrole-3-carbonitrile with at least about 1 or 2 equivalents of a sulfuryl halide, bromine or chlorine, in the presence of a solvent such as dioxane, THF, acetic acid or a chlorinated hydrocarbon solvent. For preparation of a monohalo pyrrole-3-carbonitrile use of about 1 equivalent of the halogenating agent is required; whereas, preparation of a dihalo pyrrole-3-carbonitrile requires 2 to 3 equivalents of said halogenating agent. When sulfuryl chloride or sulfuryl bromide is used the reaction is generally conducted at a temperature below about 40° C. and preferably between about 0° and 30° C., but when elemental bromine is employed, the reaction is usually conducted at about 30°–40° C. Other effective halogenating agents that may be employed in these reactions include sodium hypochlorite, t-butylhypochlorite, N-bromosuccinimide, N-iodosuccinimide and the like. The reaction may be illustrated as follows:

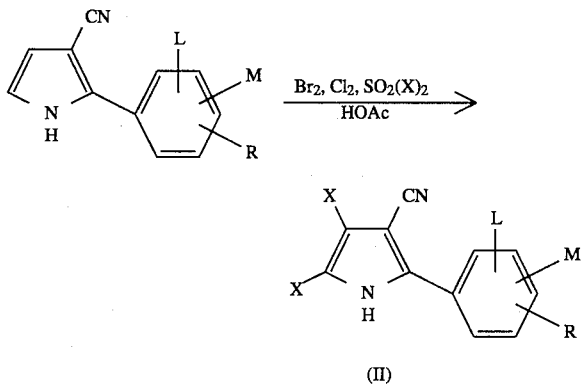

The formula II carbonitrile compounds of the present invention may also be prepared from the reaction of a substituted or unsubstituted benzoyl acetonitrile with a 2,2-di($C_1$–$C_4$ alkoxy)ethylamine in the presence of an aromatic solvent to form the α-(2,2-di($C_1$–$C_4$ alkoxy)ethylamino)-β-cyano-(substituted)styrene which is then converted to the 2-(substituted-phenyl)-pyrrole-3-carbonitrile of formula II by reaction of said β-3-cyano-(substituted)styrene compound with trifluoroacetic acid or with concentrated HCl at a temperature between about 20° and 40° C. The reactions may be illustrated as follows:

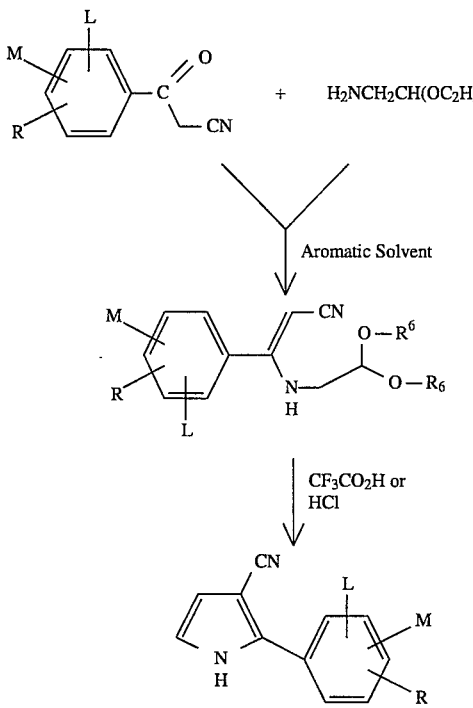

wherein $R_6$ is $C_1$–$C_4$ alkyl and L, R and M are as described above.

Also in accordance with the present invention formula II 3-nitro-2-phenylpyrrole and 3-nitro-2-(substituted)phenylpyrrole compounds can be prepared by reaction of an α-nitroacetophenone or a substituted α-nitroacetophenone with a 2,2-di($C_1$–$C_4$-alkoxy)ethylamine. The reaction is generally conducted in the presence of an inert organic solvent preferably an aromatic solvent, at an elevated temperature to give an α-(2,2-di($C_1$–$C_4$-alkoxy)ethylamino)-β-nitrostyrene or a substituted α-(2,2-di($C_1$–$C_4$-alkoxy)ethylamino)-β-nitrostyrene that is converted to the formula II 3-nitro-2-phenylpyrrole or 3-nitro-2-(substituted)phenylpyrrole by treatment with a mineral acid such as hydrochloric or hydrobromic acid. Reaction of the thus prepared nitrophenylpyrrole with sodium hypochlorite in the presence of an inert organic solvent at a reduced temperature yields the formula II 2,3-dichloro-4-nitro- 5-phenyl or 5-(substituted)phenylpyrrole.

The above reactions may be illustrated as follows:

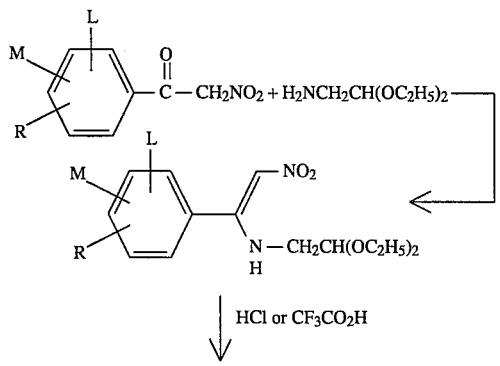

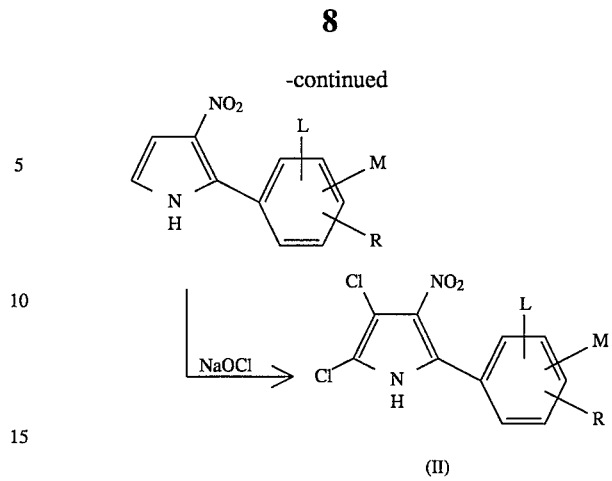

In addition to the several methods described in the literature for preparing substituted and unsubstituted benzoyl acetonitriles, surprisingly we have found that these compounds may also be prepared by reacting an appropriately substituted benzoyl halide with an alkali metal hydride and an alkyl cyanoacetate, such as t-butyl cyanoacetate, to yield the corresponding t-butyl(benzoyl or substituted benzoyl)cyanoacetate. These reactions may be illustrated as follows:

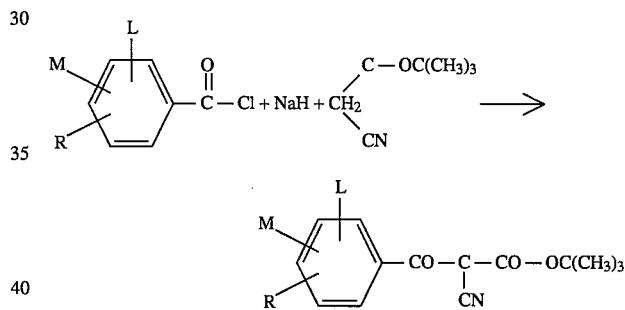

The thus formed cyanoacetate ester can then be converted to a substituted or unsubstituted benzoyl acetonitrile by heating the compound in toluene containing p-toluene sulfonic acid. The reaction may be illustrated as follows:

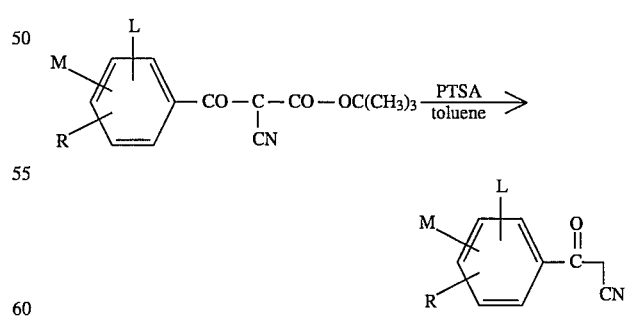

Examples of the t-butyl(benzoyl and substituted benzoyl acetonitriles) used in the above reactions are shown in Tables below.

t-Butyl (benzoyl and Substituted benzoyl)cyanoacetates

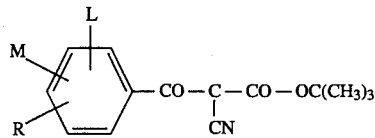

| L | M | R | mp °C. |
|---|---|---|---|
| H | 3-Cl | 4-Cl | 91–94 |
| H | H | 4-OCF$_3$ | 81–84 |
| H | H | 4-Br | 113–115 |
| H | H | 4-CF$_3$ | 146–147 |
| H | H | 4-F | 98–100 |
| H | H | 4-CN | 127–128 |
| H | H | 4-CF$_3$CH$_2$O | 136–139 |
| H | H | 4-CH$_3$SO$_2$ | 127–129 |
| H | 3-F | 4-F | 91–94 |
| H | H | 4-CH$_3$S | 117–119.5 |
| H | H | 4-CHF$_2$CF$_2$O | 92–94 |
| 3-Cl | 5-Cl | 4-CH$_3$O | — |

Benzoyl Acetonitriles

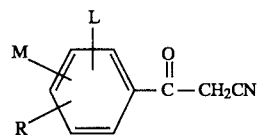

| L | M | R | mp °C. |
|---|---|---|---|
| H | H | 4-Cl | 128.5–129.5 |
| H | 3-Cl | 4-Cl | 105–107 |
| H | H | 2-C | 153–55 |
| H | H | 4-OCF$_3$ | 79–81 |
| H | H | 4-CF$_3$ | 44–45 |
| H | 2-Cl | 4-Cl | 66–67 |
| H | H | 3-Cl | 80–83 |
| H | H | 4-CN | 126–128 |
| H | H | 4-F | 78–80 |
| H | H | 4-SO$_2$CH$_3$ | 129–132 |
| H | 3-F | 4-F | 74–75 |
| H | H | 3-CF$_3$ | 58–60 |
| H | H | 4-CH$_3$ | 103.5–106 |
| H | H | 4-NO$_2$ | 119–124 |
| 3-Cl | 5-Cl | 4-OCH$_3$ | — |

Preparation of N-substituted formula I arylpyrroles can be achieved by reaction of the appropriately substituted formula I arylpyrrole, wherein A is hydrogen and L, M, R, W, X and Y are as described above, with an appropriate alkylating agent and a suitable base, for example, C$_1$–C$_4$ alkylOCH$_2$Cl and potassium t-butoxide. This reaction provides an arylpyrrole having the same substituents as the starting material, but in addition is substituted on the nitrogen with C$_1$–C$_4$ alkoxymethyl. In a similar reaction cyanogen bromide is substituted for the brominated hydroxy C$_1$–C$_4$ alkyl and yields the formula I arylpyrrole with a carbonitrile substituent on the nitrogen. The reactions may be illustrated as follows:

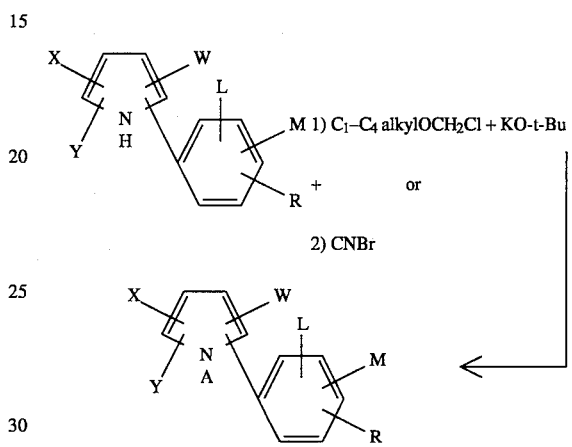

wherein L, M, R, W, X and Y are as described for formula I above and A is 1) C$_1$–C$_4$ alkoxymethyl or 2) CN.

Preparation of 2-phenylpyrrole 3,4-dicarbonitrile, 2-bromo-5-phenylpyrrole-3,4-dicarbonitrile and substituted phenyl derivatives thereof can be obtained by reaction of fumaronitrile with bromine in the presence of a chlorinated hydrocarbon such as chloroform at an elevated temperature to yield bromofumaronitrile. The thus formed bromofumaronitrile is then reacted with N-(trimethylsilyl)methyl-5-methyl-benzene-thioimidate or a substituted derivative thereof, in the presence of hexamethylphosphoramide at an elevated temperature to yield the 2-phenylpyrrole-3,4-dicarbonitrile. Bromination of the thus prepared 3,4-dicarbonitrile yields the 2-bromo-5-phenylpyrrole-3,4-dicarbonitrile or the substituted phenyl derivative if the substituted N-(trimethylsilyl)methyl-5-methyl-benzene-thioimidate is used in the previous reaction. The reaction may be illustrated as follows:

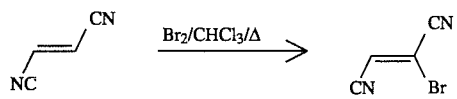

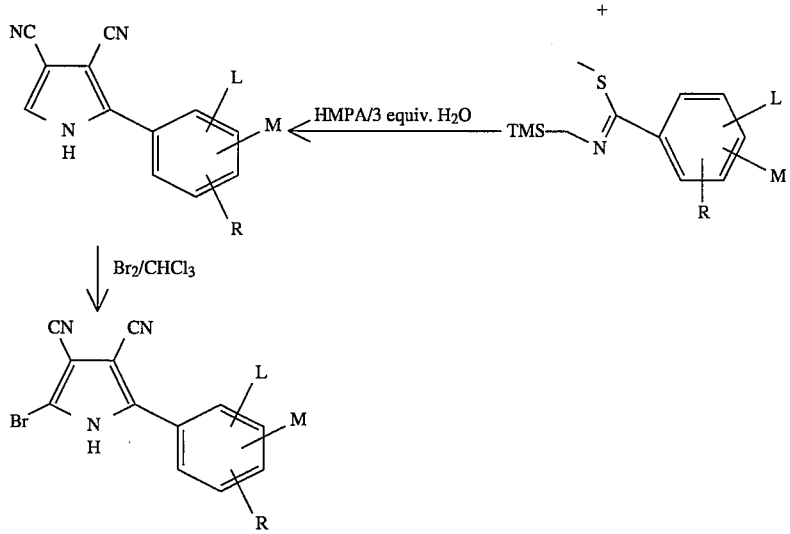

-continued

In order to facilitate a better understanding of the present invention, the following examples are presented primarily for the purpose of illustrating certain more specific details thereof. The invention is not to be deemed limited thereby except as defined in the claims.

EXAMPLE 1

Evaluation of test compounds as nematicidal agents

Cultures of *C. elegans* (Bristol strain from J. Lewis) are maintained on *E. coli* lawns on NG Agar Plates at 20° C. New cultures are established weekly.

Nematodes for testing are washed from 4–5 day old cultures using Fresh Ascaris Ringers Solution (FARS). The worms are further washed with FARS, containing gentamycin, to reduce bacterial contamination and centrifuged to separate worms from wash solution. This procedure is repeated three times. The washed worms are then added to *C. brigassae* Maintenance Medium (CbMM), from GIBCOa to which is added gentamycin (600 units/ml) and mycostatin (0.5 mg/ml).

Compounds are dissolved in acetone and made up to volume with equal parts of water. The final test concentration of each compound in the mixture is 150 ppm. The test material is micropipetted (25 ul) into a single well of a 96-well sterile tissue culture plate (COSTAR)[b] and the solvent allowed to evaporate. These "treated" plates are used immediately or stored in a refrigerator without apparent adverse effects on the compounds.

A freshly prepared volume (50 ug) of *C. elegans* in CbMM is micropipetted into each treated well and several control wells per plate. Culture plates are incubated at 20° C.

Observations for efficacy are made under a dissecting microscope at 4 and 24 hours post-immersion. Immediately prior to reading the plate, it is gently tapped to stimulate the movement of the worms. Activity is judged based on the drug effects on motility of the adults and larvae. The criteria are as follows: 9= complete kill, 8=no motility, 7= markedly reduced motility in approximately 95% of worms, 6= reduced motility, 5= slightly reduced motility, 0= normal motility, same as controls. Other factors indicating activity are easily noted such as death, rigor mortis, contraction, coiling, paralysis, abnormal twitching, reduced worm population in 48 hours and other deviation from normal behavior.

PROCEDURE FOR CAENORHABDITIS ELEGANS ASSAY

Day 0 .Inoculate *E. Coli*-NG Agar Dish With 30–40 *C. Elegans* .Incubate At 20° C.

Day 4 .Harvest New *C. Elegans* Population .Wash With Antibiotics .Transfer To CbMM .Add *C. Elegans* (25–100 UL) To "Medicated" Wells[a] .Observe for Activity at 4 hours Post-Immersion Day 5 .Observe For Activity

[a]Medicated Wells May Be Prepared Fresh or Earlier and Stored In Refrigerator

Data obtained in these tests are reported in Table I below.

TABLE I

| Evaluation of Arylpyrrole Activity Against *C. Elegans* | |
|---|---|
| Compound | Rating Against *C. Elegans* 150 ppm |
| 2,3-Dichloro-5-(P-chloro-phenyl)-4-nitropyrrole | 9 |
| 2,5-Dichloro-3-(3,4-dichloro-phenyl)-4-nitropyrrole | 9 |
| 2,3-Dichloro-5-(3,4-dichloro-phenyl)-4-nitropyrrole | 9 |
| 2-(P-bromophenyl)-4,5-dichloro-3-nitropyrrole | 9 |
| 2,3-Dichloro-4-nitro-5-($\alpha,\alpha,\alpha$-Trifluoro-2-tolylpyrrole | 9 |
| 3-Nitro-4-phenylpyrrole | 9 |
| 4,5-Dibromo-2-(O-chlorophenyl)-pyrrole-3-carbonitrile | 9 |
| 4,5-Dichloro-2-($\alpha,\alpha,\alpha$-trifluoro-P-tolylpyrrole-3-carbonitrile | 9 |
| 4,5-Dibromo-2-($\alpha,\alpha,\alpha$-trifluoro-P-tolyl)pyrrole-3-carbonitrile | 9 |
| 4,5-Dibromo-2-(P-nitrophenyl)-pyrrole-3-carbonitrile | 9 |
| 4,5-Dichloro-2-(P-nitrophenyl)-pyrrole-3-carbonitrile | 9 |
| 1-Benzyl-4,5-dibromo-2-($\alpha,\alpha,\alpha$-trifluoro-P-tolyl)pyrrole-3-carbonitrile | 9 |

TABLE I-continued

Evaluation of Arylpyrrole Activity Against *C. Elegans*

| Compound | Rating Against *C. Elegans* 150 ppm |
|---|---|
| 4,5-Dichloro-2-(P-cyanophenyl)-pyrrole-3-carbonitrile | 9 |
| 4,5-Dibromo-2-[P-(methylsulfonyl)phenyl]-pyrrole-3-carbonitrile | 9 |
| 4,5-Dibromo-2-(P-cyanophenyl)-pyrrole-3-carbonitrile | 9 |
| 4,5-Dichloro-2-(3,4-dichlorophenyl)-1[2-(methylthio)ethyl]pyrrole-3-carbonitrile | 9 |
| 1-Alkyl-4,5-dichloro-2-(3,4-dichlorophenyl)pyrrole-3-carbonitrile | 9 |
| 5-(3,4-Dichlorophenyl)-pyrrole-3-dicarbonitrile | 9 |
| 3-(P-chlorophenyl)pyrrole-2-carbonitrile | 9 |
| 4-Bromo-2-(3,4-Dichlorophenyl)-5-nitropyrrole-3-carbonitrile | 9 |
| 3,4-Dibromo-5-(3,4-dichlorophenyl)-pyrrole-2-carbonitrile | 9 |
| 2-(P-chlorophenyl)-5-nitropyrrole-3-carbonitrile | 9 |
| 4-Bromo-2-(P-chlorophenyl)-5-(trifluoromethyl)pyrrole-3-carbonitrile | 9 |
| 3-Bromo-5-(P-chlorophenyl)pyrrole-2,4-dicarbonitrile | 9 |
| 5-(3,4-Dichlorophenyl)-4-nitro-pyrrole-2-carbonitrile | 9 |
| 3-Bromo-5-[P-(trifluoromethoxy)phenyl]-pyrrole-2-4-dicarbonitrile | 9 |
| Bromo-5-(3,4-dichlorophenyl)-4-nitropyrrole-2-carbonitrile | 9 |
| 3,5-Dibromo-4-(P-chlorophenyl)-pyrrole-2-carbonitrile | 9 |
| 4-Bromo-2-(3,4-dichlorophenyl)-5-(trifluoromethyl)pyrrole-3-carbonitrile | 9 |
| 4-Bromo-2-(P-chlorophenyl)-1-(ethoxymethyl)-5-(trifluoromethyl)-pyrrole-3-carbonitrile | 9 |
| 5-(α,α,α-trifluoro-tolyl)-pyrrole-3-carbonitrile | 9 |
| 4-Bromo-1-(ethoxymethyl)-5-(trifluoromethyl)-2-(α,α,α-trifluoro-P-tolyl)-pyrrole-3-carbonitrile | 9 |
| 4-Bromo-2-(3,4-dichlorophenyl)-1-(ethoxymethyl)-5-(trifluoromethyl)-pyrrole-3-carbonitrile | 9 |
| 2-(3,4-dichlorophenyl)-3-nitro-5-trifluoromethyl)pyrrole | 9 |
| 4-Bromo-5-nitro-2-(α,α,α-trifluoro-P-tolyl)pyrrole-3-carbonitrile | 9 |
| 2,4-Dibromo-5-(α,α,α-trifluoro-P-tolyl)pyrrole-3-carbonitrile | 9 |
| 4-Bromo-2-(2,4-dichlorophenyl)-5-(trifluoromethyl)pyrrole-3-carbonitrile | 9 |
| 4,5-Dichloro-1-(1-ethoxymethyl)-2-(α,α,α-trifluoro-P-tolyl)-pyrrole-3-carbonitrile | 9 |
| 4,5-Dichloro-2-(3,4-dichlorophenyl)-1-[2-(dimethylamino)ethyl]pyrrole-3-carbonitrile | 9 |
| 4-Bromo-2-(2,4-Dichlorophenyl)-1-(ethoxymethyl)-5-(trifluoromethyl)pyrrole-3-carbonitrile | 9 |
| 1-Benzyl-3-bromo-5-(P-chlorophenyl)pyrrole-2,4-dicarbonitrile | 9 |
| 4-Bromo-2-(m-nitrophenyl)-5-(trifluoromethyl)pyrrole-3-carbonitrile | 9 |
| 5-Bromo-3-(P-chlorophenyl)-pyrrole-2,4-dicarbonitrile | 9 |
| 3-(P-chlorophenyl)-4-nitro-pyrrole | 9 |
| 3-Bromo-5-(P-chlorophenyl)-4-cyano-2-(trifluoromethyl)-pyrrole-1-acetonitrile | 9 |
| 4-Bromo-2-(P-chlorophenyl)-1-(1-methoxymethyl)-5-(trifluoromethyl)pyrrole-3-carbonitrile | 9 |
| 4,5-Dichloro-1-(hydromethyl)-2-(α,α,α-trifluoro-P-tolyl) | 9 |
| 2,3,-Dichloro-4-cyano-5-(α,α,α-trifluoro-P-tolyl)pyrrole-1-acetonitrile | 9 |
| 4,5-Dichloro-1-(methoxyethyl)-2-(α,α,α-trifluoro-P-tolyl)pyrrole-3-carbonitrile | 9 |
| 3-Nitro-2-phenyl-4,5-bis(trifluoromethyl)pyrrole | 9 |
| 4-Bromo-3-(P-chlorophenyl-5-(trifluoromethyl)pyrrole-3-carbonitrile | 9 |
| 4-Phenyl-5-(trifluoromethyl)pyrrole-3-carbonitrile | 9 |
| 2-Bromo-4-phenyl-5-(trifluoromethyl)pyrrole-3-carbonitrile | 9 |
| 2-Bromo-4-(P-chlorophenyl)-5-(trifluoromethyl)pyrrole-3-carbonitrile | 9 |
| 2-(P-bromophenyl)-3,5-dimitropyrrole | 9 |
| 2-(P-chlorophenyl)-4,5-bis(trifluoromethyl)pyrrole-3-carbonitrile | 9 |
| 3-(P-chlorophenyl)-2-(trifluoromethyl)pyrrole | 9 |

EXAMPLE 2

Evaluation of Arylpyrroles against Psoroptes cuniculi

On the day prior to the test initiation the drugs to be evaluated are dissolved in acetone and diluted to the desired concentrations. The concentration is calculated so that 400 μl contains the amount of test compound to be placed on each filter paper. 400 μl of this solution is pipetted onto a top (3.7 cm dia.) and bottom (3.5 cm dia.) filter paper disks which are then placed on a ceramic plate to dry. There is a rough and smooth side to the filter paper. Drug should be applied to the rough side which is placed up while drying. When dry the two disks are placed in a Petri dish with the rough sides facing in, separated by one 3 mm glass bead. Dishes are held at room temperature overnight if done the day before the test.

Scab (containing mites) is collected from the ears of infested rabbits the morning of the test. This material is placed in a large Petri dish under an illuminated magnifier. Mites crawl out of the scab and are easily collected on the point of a dissecting needle or one prong of a pair of fine forceps. The top filter paper in each dish is removed and 12 mites are placed on the bottom disk and the top paper replaced. Before replacing the top of the Petri dish the rim of the dish is smeared with Vaseline to trap any escaping mites.

For evaluation tests there are generally 4 replicates of each dose which are counted at 24 hours. After mites are added to the dishes, the dishes in each replicate are placed in a tray which is then placed in a plastic bag with several wet towels and held at room temperature.

After 24 hours dishes are examined under a dissecting scope. Each dish is opened carefully and the top filter paper removed and saved. A ½ cm circle is drawn on the bottom filter paper and the paper gently wet in the area of the circle. All mites from the dish are transferred into the wet circle area and counted. The top cover is replaced on each dish and the dishes set aside for at least 15 minutes. After standing the dishes are examined and the mites remaining on the circle counted. These mites are dead. Percent mortality of the mites is then calculated for each treatment. These data are reported in Table II below.

TABLE II

Evaluation of arylpyrroles against *Psoroptes cuniculi* (Rabbit Ear Mite)

| Compound | μg/cm² | 24 hour % Mortality |
|---|---|---|
| 2,3-Dichloro-5-(P-chloro-phenyl)-4-nitropyrrole | 10.0 | 91 |
|  | 4.0 | 52 |
| 3-Bromo-5-(P-chloro-phenyl)pyrrole-2,4-dicarbonitrile | 4.0 | 48 |
| 2,4-Dibromo-5-(P-chloro-phenyl)pyrrole-3-carbonitrile | 4.0 | 11 |
| 2-(2,4-Dichloro-5-fluoro-phenyl)pyrrole-3-carbonitrite | 4.0 | 73 |
| 4,5-Dichloro-2-(3,4-dichlorophenyl)pyrrole-3-carbonitrile | 10.0 | 33 |
| 2-(3,4-Dichlorophenyl)-3-nitro-(trifluoromethyl)-pyrrole | 4.0 | 100 |
| 4-Bromo-2-(P-chloro-phenyl)-1-(ethoxymethyl)-5-(trifluoromethyl)pyrrole-3-carbonitrile | 4.0 | 76 |
| 4-Bromo-2-(P-bromophenyl)-1-(ethoxymethyl)-5-(trifluoromethyl)pyrrole-3-carbonitrile | 4.0 | 31 |
|  | 16.0 | 100 |
| 4,5-Dichloro-1-(ethoxy-methyl)-2-(α,α,α-trifluoro-P-tolyl)pyrrole-3-carbonitrite | 4.0 | 92 |
|  | 1.0 | 100 |
|  | 0.1 | 20 |
|  | 0.01 | 48 |
| 4,5-Dichloro-1-(ethoxy-methyl)-2-[P-(trifluoro-methoxy)phenyl]pyrrole-3-carbonitrile | 4.0 | 100 |
| 2-(3,4-Dichlorophenyl)-1-(ethoxymethyl)-3-nitro-5-(trifluoromethyl)pyrrole | 4.0 | 92 |
| 2,3-Dichloro-4-cyano-5-(α,α,α-trifluoro-P-tolyl)-pyrrole-1-acetonitrile | 4.0 | 77 |

EXAMPLE 3

Evaluation of Arylpyrroles against the larval stages of the Dogtick, *Dermacentor variabilis*

The test procedure used herein is the same procedure described in Example 2, for evaluating the arylpyrroles for control of *Psoroptes cuniculi* the Rabbit Ear Mite, with the following exceptions:

(1) Unfed larval ticks are obtained from egg masses laid by gravid female ticks removed from dogs and each replicate receives ticks from the same egg mass;

(2) Ticks survive longer than mites in the Petri dishes, thus readings are made 48 hours or longer after the test is initiated; and (3) When reading the test it may be necessary to blow on the ticks to stimulate their movement.

Data obtained are reported in Table III below.

TABLE III

Evaluation of Arylpyrroles against the larval stages of the Dogtick, *Dermacentor variabilis*

| Compound | μg/cm² | % mortality @ 48 hour |
|---|---|---|
| 2,3-Dichloro-5-(P-chloro-phenyl)-4-nitropyrrole | 10.0 | 58 |
| 4,5-Dichloro-2-(3,4-dichloro-phenyl)pyrrole-3-carbonitrile | 10.0 | 40 |
| 4-Bromo-2-(P-chlorophenyl)-1-(ethoxymethyl)-5-(trifluoro-methyl)pyrrole-3-carbonitrile | 10.0 | 100 |
|  | 5.0 | 100 |
|  | 4.0 | 83 |
|  | 1.0 | 77 |
| 4,5-Dichloro-1-(ethoxymethyl)-2-(α,α,α-trifluoro-P-tolyl)-pyrrole-3-carbonitrile | 10.0 | 97 |
|  | 5.0 | 100 |
|  | 1.0 | 52 |
| 4,5-Dichloro-1-methyl-2-[P-(trifluoromethoxy)phenyl]-pyrrole-3-carbonitrile | 10.0 | 55 |

EXAMPLE 4

Evaluation of Arylpyrrole Compounds against *Ctenocephalides felis* the cat flea This test is conducted in the same manner as the mite filter paper test described in Example 2 with the following exceptions:

(1) Only one filter paper is used on the bottom of the dish;

(2) Unfed fleas that have emerged from pupae within the last 24 hours are used for the test. Fleas are initially collected in glass vials and then temporarily immobilized by placing the vials in ice. Once the fleas are no longer active, vials are opened and fleas dumped into Petri dishes. The number of fleas per dish will vary but generally contain 8–12 fleas.

(3) Dishes are held for 24 hours until the mortality counts are made;

(4) Edges of the Petri dish are sealed with Scotch tape to prevent escape of the fleas; and (5) Dishes are not opened when test is read but fleas are observed under dissecting scope in the dishes. Some fleas will move under the filter paper so dish should be inverted to check. Fleas are considered dead if they cannot remain upright and jump.

Data obtained are reported in Table IV below.

TABLE IV

Evaluation of Arylpyrrole Compounds against *Ctenocephalides felis* the cat flea

| Compound | μg/cm² | 24 hour % Mortality |
|---|---|---|
| 3-Bromo-5-(P-chlorophenyl)-pyrrole-2,4-dicarbonitrile | 20.0 | 47 |
| 2-(3,4-Dichlorophenyl)-3- | 20.0 | 73 |

TABLE IV-continued

Evaluation of Arylpyrrole Compounds against
*Ctenocephalides felis* the cat flea

| Compound | μg/cm$^2$ | 24 hour % Mortality |
|---|---|---|
| nitro-5-(trifluoromethyl)-pyrrole | | |
| 4,5-Dichloro-1-(ethoxy-methyl)-2-(α,α,α-trifluoro-P-tolyl)pyrrole-3-carbonitrile | 20.0 | 71 |

EXAMPLE 5

Evaluation of Aryl pyrrole compounds against
Newly emerged Housefly Larvae

In this test system newly emerged housefly larvae are grown on an undefined medium of fermented whole milk and dried beef blood. Compounds are added to the milk and activity is determined by the failure of larvae to pupate.

The test is run in 1 oz. plastic medicine cups. Paper toweling is cut in pieces approximately 3.5×10 cm. Three of these pieces are folded accordion style and placed in each paper cup. A piece of masking tape is placed on the outside of the cup to facilitate numbering. Cups should be prepared prior to the day the test is to begin.

Newly hatched housefly larvae are obtained on the morning the test is to begin. The eggs are laid the night before and larvae usually begin to hatch by 9–10 AM the following morning.

Twenty-four hours before the initiation of the test, one half gallon of whole milk is divided into 5 1-liter beakers and placed in an incubator at 39° C.

The morning of the test, one 250 ml beaker is labeled for each treatment. The fermented milk is removed from the incubator, stirred and poured into each of the small beakers. The beakers are then returned to the incubator and 1–2g of dried beef blood added to each beaker to distribute blood which will not dissolve. The beakers are again returned to the incubator.

Doses of compounds are calculated so that 0.1 ml contains the amount of compound to be added to 100 ml of milk. Compounds should be dissolved in acetone. 100μl of acetone is added to each control beaker.

Each beaker is removed from incubator and placed on a magnetic stirrer. The compound is added and thoroughly mixed. Then 20 ml portions are removed and added to labelled test cups (4 reps/treatment). Cups are placed in stainless steel tray until all are prepared. Once prepared cups are held for 24 hours if fly eggs do not hatch on time. The tray containing the cups are then placed in a plastic bag and maintained at room temperature.

The media that the fly eggs are laid in is spread out in a green or black pan so that larvae can be observed. Working under an illuminated magnifier 20 larvae are transferred into each cup using a fine paint brush. Each cup is then sealed in a Zip-Loc sandwich bag with a few pinholes in it.

Bags containing cups are placed on a flat tray and placed in a 27° C. incubator for one week. The majority of the larvae will have pupated at this point.

Trays are then removed from the incubator and the number of pupae in each bag recorded. The paper toweling is removed and examined closely for any pupae that have remained in the cups. Most of the pupae will be loose in the bag. A note is also made of any dead or live developed larvae. If there are larvae that appear capable of pupating, the bag may be returned to the incubator for a day to see if they will pupate.

The percent development of pupae is then calculated. The final results are expressed as a percent inhibition of pupation and are corrected for control mortality by using Abbott's formula. Data obtained are reported below in Table V.

TABLE V

Evaluation of arylpyrrole compounds against newly
hatched Housefly Larvae

| Compound | Conc ppm | % Inhibition of pupation |
|---|---|---|
| 3-Bromo-5-(P-chlorophenyl)-pyrrole-2,4-dicarbonitrile | 10.0 | 100 |
| | 1.0 | 0 |
| 2-(3,4-Dichlorophenyl)-3-nitro-5-(trifluoromethyl)-pyrrole | 10.0 | 100 |
| 4-Bromo-2-(P-chlorophenyl)-1-(ethoxymethyl)-5-(trifluoromethyl)pyrrole-3-carbonitrile | 10.0 | 99 |
| | 5.0 | 38 |
| | 2.5 | 0 |
| | 1.0 | 15 |
| 4,5-Dichloro-1-(ethoxymethyl)-2-(α,α,α-trifluoro-P-tolyl)-pyrrole-3-carbonitrile | 10.0 | 64 |
| 2,3-Dichloro-4-cyano-5-(α,α,α-trifluoro-P-tolyl)-pyrrole-1-acetonitrile | 10.0 | 100 |

EXAMPLE 6

Evaluation of arylpyrroles for control of Helminths
in warm-blooded animals

Each test generally consists of 75 infected gerbils, randomly distributed 2 or 3 per cage (the number of animals per cage is consistent within a specific experiment). Generally, there are 8–9 untreated control gerbils (3–4 cages) per test. The remaining cages are assigned a treatment, usually 1 cage per compound or dose.

Compounds administered in diet are fed for 4 days. Animals treated by gavage or injection are generally treated on only i day (usually day 7).

In accordance with this test, gerbils are each orally infected by gavage, with about 400 *Trichostrongylus colubriformis* infective larvae of sheep origin. The infected animals are then permitted to feed and drink ad libitum for six days. On day 7 the infected gerbils are randomly placed in rodent cages 2 or 3 animals per cage. The animals in each cage are weighed and the feed for each cage weighed. If the treatment to be evaluated is medicated feed, said medicated feed is offered on day 7 and continued through day 11 of the trial. If the treatment to be evaluated is a single oral dose or a parenteral treatment, the animals are given the medication by gavage or injection on day 7 and receive unmedicated feed and water through day 11 of the trial. On day 11 the animals and their feed are weighed. Thereafter the animals are euthanized by $CO_2$ inhalation and their small intestines removed, inverted on application sticks and incubated in tap water at 39° C. for 1–5 hours. The sticks and intestines are then discarded and the worms from each treatment counted to determine the % mortality of the worms as compared to untreated controls. Data obtained are reported in Table VI below.

TABLE VI

Evaluation of Formula I arylpyrrole compounds against *T. colubriformis* in Gerbils

| Compound | PPM in Diet | % Helminth removal |
|---|---|---|
| 3-Bromo-5-(P-chlorophenyl)- pyrrole-2,4-dicarbonitrile | 500 | 54 |
| | 500 | 36 |
| | 500 | 50 |
| Single oral dose | | |
| | 25 mg/kg | 18 |
| | 10 mg/kg | 25 |
| 4-Bromo-2-(P-chlorophenyl)- 1-(ethoxymethyl)-5-(trifluoro- Methyl)-2-(α,α,α-trifluoro-P- tolyl)pyrrole-3-carbonitrile | 500 | 29 |
| 4-Bromo-1-(ethoxymethyl)- 5-(trifluoromethyl)pyrrole- 3-carbonitrile | 500 | 13 |
| 4-Bromo-2-(3,4-dichlorophenyl)- 1-(ethoxymethyl)-5-(trifluoro- methyl)pyrrole-3-carbonitrile | 500 | 15 |
| 4-Bromo-2-(3,4-dichloro- phenyl)-1-(ethoxymethyl)-5- (trifluoromethyl)pyrrole-3- carbonitrile | 500 | 28 |
| 4,5-Dichloro-1-(hydroxy- methyl)-2-(α,α,α-trifluoro-P- tolyl)-3-carbonitrile acetate ester | 500 500 | 37 8 |
| 3-Nitro-2-phenyl-4,5- bis(trifluoromethyl)pyrrole | 500 | 42 |

EXAMPLE 7

Preparation of 2-Phenylpyrrole-3-carbonitrile

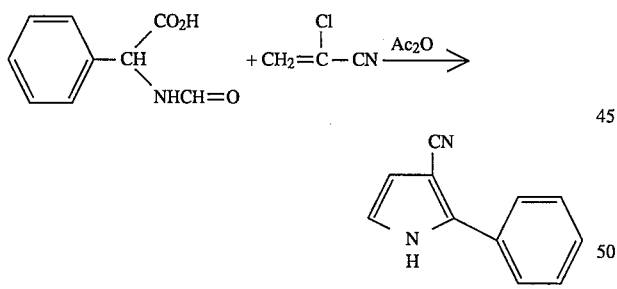

The following procedure is similar to the method given in JOC, 43, 4273–6 (1978). A stirred mixture of 30.0 g of N-formyl-phenylglycine is heated at 90° C. for 1.5 hours. The clear yellow reaction solution is concentrated in vacuo to give 42.5 g of an oily brownish orange semi-solid. Material partially purified by chromatography on silica gel is shown by the proton NMR spectrum to be a mixture of 73% 2-phenylpyrrole- 3-carbonitrile and 27% 2-phenyl-3-cyano-5-methylpyrrole. Recrystallization once from chloroform and twice from 1,2-dichloroethane gives 1.69 g of an off-white solid which proton NMR shows it to be 96% 2-phenylpyrrole-3-carbonitrile, mp 148°–152° C.

EXAMPLE 8

Preparation of 4,5-Dichloro-2-phenylpyrrole-3-carbonitrile and 5-chloro-2-phenylpyrrole-3-carbonitrile

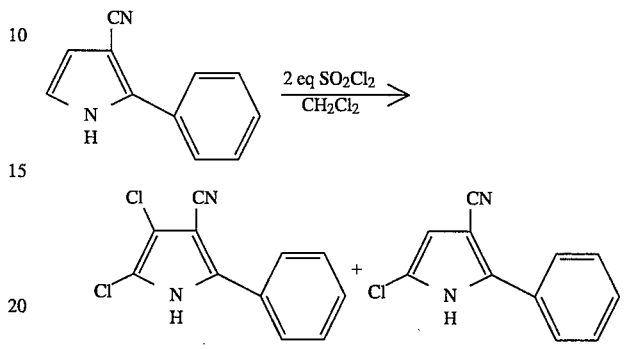

To a stirred ice-water cooled solution of 2.00 g (11.9 mmol) of 2-phenyl-3-cyanopyrrole in 80 mL of methylene chloride is added dropwise over a period of 5 min., 1.90 mL (3.19 g, 23.6 mmol,) of sulfuryl chloride by means of a syringe. Throughout the addition the temperature is kept between 5° C. and 10° C. Stirring at 5°–10° C. is continued for 90 minutes. The reaction mixture is vacuum filtered to remove a precipitated solid (1.28 g) identified as 5-chloro-2-phenylpyrrole-3-carbonitrile, mp 192.5°–195° C. The filtrate is diluted with 400 mL of ethyl acetate, washed twice with 200 mL of water, dried (sodium sulfate), treated with charcoal, filtered, and then concentrated in vacuo to give (after slurrying of the residue with hexane) 0 60 g (21.3% yield) of a pink-purple solid. This solid is recrystallized from 5 mL of hot acetone to give 0.32 g (9% yield) of 4,5-dichloro- 2-phenylpyrrole-3-carbonitrile as an orangish brown solid, mp 254°–255° C.

EXAMPLE 9

Preparation of p-Chloro-β-[(formylmethyl)amino]cinnamonitrile, diethyl acetal

A stirred solution of 250.00 g (1.39 mol,) of p-chlorobenzoylacetonitrile, 203 mL (185.95 g, 1.39 mol) of 2,2-diethoxyethylamine, and 1300 mL of dried toluene is heated at reflux for 20 hours. Water is collected in a Dean-Stark trap (23 8 mL, 95.2% theory). The hot cloudy dark brown solution with a large amount of undissolved solids is filtered through diatomaceous filter aid. After dilution with 200 mL of EtOAc, the solution is filtered through a 7 cm×13.5 cm column of silica gel. The filtrate is concentrated in vacuo to give 354.38 g (86.4% crude yield) of a clear dark oil which slowly solidifies. This solid is recrystallized from hot cyclohexane to give 324.26 g (79.1% yield) of a waxy orange solid. NMR of this product shows it to be composed of 78% (Z) and 23% (E) isomeric mixture of p-chloro-β-[(formylmethyl)amino]cinnamonitrile, diethyl acetal, mp 60°–72° C.

EXAMPLE 10

Preparation of
2(p-Chlorophenyl)-pyrrole-3-carbonitrile

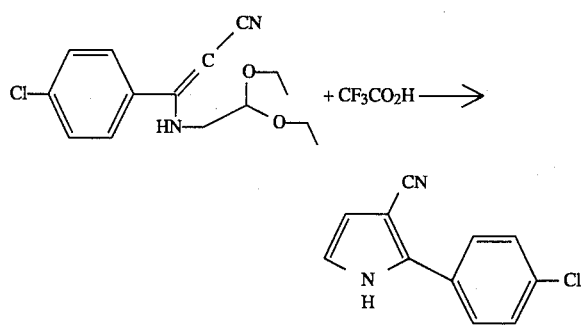

To 108 mL of trifluoroacetic acid stirred at 23° C. is added 54.00 g (0,183 mol) of solid p-chloro-β-[(formylmethyl)amino] cinnamonitrile, diethyl acetal over a period of 45 minutes. This addition produced an exotherm to 38° C. and, 32 minutes into the addition, a solid started to precipitate. After stirring at room temperature for 30 minutes, the reaction mixture is vacuum filtered and the collected solid is washed first with trifluoroacetic acid, secondly with an ethyl acetate-hexane mixture, and finally with hexane. The yield is 16.83 g (45.4%) of an off-white solid, mp 165°–166° C.

Use of the above procedure as shown or with the substitution of concentrated hydrochloric acid for trifluoroacetic acid affords the following compounds:

| M and/or R | mp °C. | Acid Used |
|---|---|---|
| 4-Cl | 165–166 | conc. HCl,CF$_3$COOH |
| 3,4-di-Cl | 216–221 | CF$_3$COOH |
| 2-Cl | 156–157 | CF$_3$COOH |
| 4-OCF$_3$ | 143–145 | CF$_3$COOH |
| 4-CF$_3$ | 179–180 | CF$_3$COOH |
| 2,4-di-Cl | 197–199 | CF$_3$COOH |
| 3-Cl | 150–156 | CF$_3$COOH |
| 4-CN | 210–212 | CF$_3$COOH |
| 4-F | 167–170 | conc. HCl |
| 4-SO$_2$CH$_3$ | 221–221.5 | CF$_3$COOH |
| 3,4-di-F | 173–175.5 | CF$_3$COOH |
| 3-CF$_3$ | 166–168 | CF$_3$COOH |
| 4-COOCH$_3$ | 155.5–158 | CF$_3$COOH |
| 4-CH$_3$ | 117–137 | CF$_3$COOH |
| 4-NO$_2$ | 174–177 | CF$_3$COOH |

EXAMPLE 11

Preparation of
4,5-Dichloro-2-(p-chlorophenyl)pyrrole-3-carbonitrile

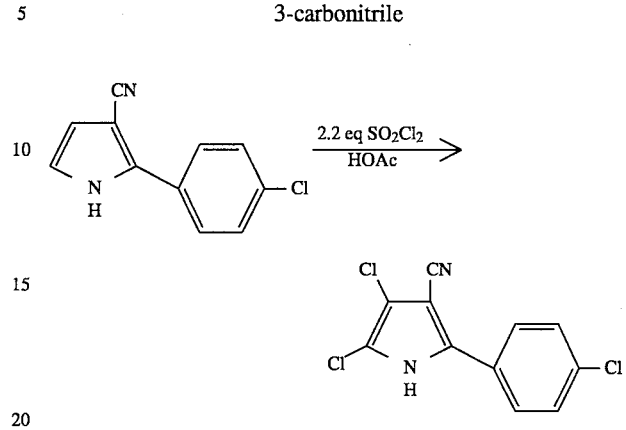

To a stirred solution of 16.83 g (83.1 mmol) of 2-(P-chlorophenyl)pyrrole-3-carbonitrile in 450 mL of glacial acetic acid at 36° C. is added dropwise 14.7 mL (24.70 g, 183.0 mmol) of sulfuryl chloride over a period of 18 minutes. The addition produces a slight exotherm to 39° C. and, after another 16 minutes, the reaction mixture is vacuum filtered. The collected solids are washed first with acetic acid and then with water. This solid after recrystallisation from hot ethyl acetate, melts at 259°–261° C.

EXAMPLE 12

Preparation of
4,5-Dibromo-2-(α,α,α-trifluoro-p-tolyl)-pyrrole-3-carbonitrile

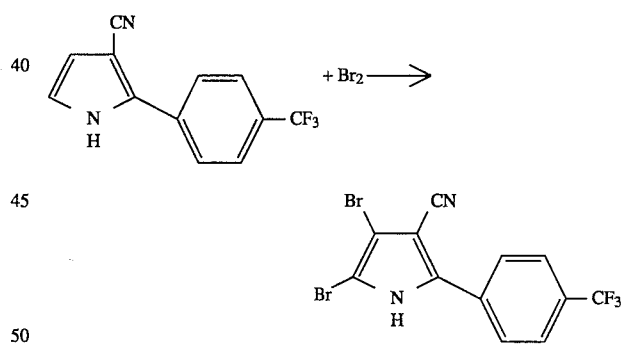

To a stirred mixture of 0.8 g of 2-(α,α,α-trifluoro-p-tolyl)pyrrole- 3-carbonitrile in 70 mL of chloroform is added 2 mL of bromine. The mixture, on stirring overnight, deposits a white solid which is collected by filtration. Thin layer chromatography (1:1 ethyl acetate-hexane) shows a single component; mp <230° C.

Following the procedures of Examples 11 and 12, but substituting the appropriately substituted phenyl-pyrrole-3-carbonitrile for 2-(α,α,α-trifluoro-p-tolyl)pyrrole- 3-carbonitrile yields the following compounds.

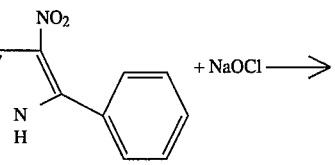

| L | M | R | X | Y | mp °C. |
|---|---|---|---|---|---|
| H | H | 4-NO₂ | Br | Br | 274–277 |
| H | H | 4-F | Cl | Cl | >220 |
| H | H | 4-F | Br | Br | >220 |
| H | H | 4-SO₂CH₃ | Cl | Cl | >230 |
| H | 3-F | 4-F | Cl | Cl | >230 |
| H | 3-F | 4-F | Br | Br | >220 |
| 2-Cl | 3-Cl | 4-Cl | Cl | Cl | |
| 2-Br | 3-Br | 4-Br | Br | Br | |
| H | H | 4-OCF₃ | Cl | Cl | 222–225 |
| H | H | 4-OCF₃ | Br | Br | 231–232 |
| H | H | 4-OCF₃ | Cl | H | |
| H | H | 4-CN | Br | Br | >230 |
| H | H | 4-CN | Cl | Cl | >240 |
| H | H | 4-SO₂CH₃ | Br | Br | >230 |
| H | H | 4-NO₂ | Cl | Cl | 246–249 |
| H | 3-Cl | 4-Cl | Br | Br | >260 |
| H | H | 3-CF₃ | Cl | Cl | >230 |
| H | H | 4-COCH₃ | Cl | Cl | 251–254 |
| H | 2,3-CH=CH— | | Cl | Cl | 244–247 |
| H | H | 4-CH₃ | Cl | Cl | 215–217 |
| H | 2-Cl | 4-Cl | Br | Br | >230 |
| H | H | 3-Cl | Cl | Cl | >230 |
| H | 2-Cl | 4-Cl | Cl | Cl | >230 |
| H | H | 4-Cl | Br | Br | 273–274 |
| H | H | 2-Cl | Br | Br | >230 |
| H | H | 4-CF₃ | Cl | Cl | >230 |
| H | H | 4-Br | Cl | Cl | >235 |
| H | H | 2-Cl | Cl | Cl | >230 |
| H | 3-Cl | 4-Cl | Cl | Cl | >235 |
| H | H | H | Cl | Cl | 254–255 |
| H | H | 4-Cl | Cl | Cl | 255–257 |
| H | H | 4-CF₃ | Br | Br | >230 |
| H | H | 4-Cl | Cl | Br | 262–263 (dec.) |
| H | H | 4-Cl | Br | Cl | 250–258 (dec.) |
| H | 3-Cl | 5-Cl | Cl | Cl | >230 |
| H | 3-Cl | 4-Cl | Cl | Br | >230 |
| 2-Cl | 4-Cl | 5-F | Cl | Cl | 207–210 |

EXAMPLE 13

Preparation of 3-Nitro-2-phenylpyrrole

Alpha-nitro acetophenone (5.7 g, 0.0345 mol) is taken up in 100 mL toluene and 4.6 g (0.0345 mol) of amino acetaldehyde diethyl acetal is added. The reactants are put into a 250 mL RB flask fitted with a Dean-Stark trap. The trap is filled with 4A molecular sieves and the mixture is heated at reflux for 18 hours. The toluene is removed in vacuo to give 8.36 g of α-(2,2-diethoxyethylamino)-β-nitrostyrene as a brown oil. To this oil is added 50 mL of concentrated HCl. As the flask is swirled the oil turns to a yellow suspension. After 10 minutes the solid is filtered to give 2.48 g of a yellow solid. Recrystallization from ether/ethylacetate/hexane gives the product as two fractions, 2.08 g of mp 190°–192° C.

EXAMPLE 14

Preparation of 2,3-Dichloro-4-nitro-5-phenylpyrrole

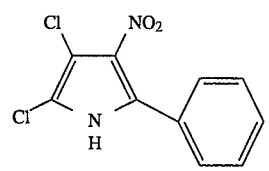

A mixture of 3-nitro-2-phenylpyrrole (1.56 g, 0.0083 mol) in 60 mL of dioxane is cooled in an ice bath while 25.9 g (0.0182 mol) of commercial sodium hypochlorite is added dropwise. After stirring for 45 minutes, the mixture is acidified with concentrated HCl. Water and Et₂O are added. The layers are separated and the top organic layer is washed with H₂O, dried over anhydrous MgSO₄ and concentrated in vacuo to give 2.21 g of yellow solid. Purification by chromatography using silica gel and eluting with increasing ratios of ethyl acetate/hexane gives, after stripping, 0.77 g of yellow solid (36%) mp 190°–190.5° C.

Following the procedures of Examples 13 and 14 above but using the appropriately substituted α-nitro-acetophenone and 2,2-di(C₁–C₄ alkoxy) ethylamine yields the substituted α-(2,2-di(C₁–C₄ alkoxy)ethylamino)-β-nitrostyrene which is then converted to 3-nitro-2-(substituted)phenylpyrrole by treatment with HCl, HBr or CF₃CO₂H. Reaction of the thus formed substituted phenylpyrrole with sodium hypochlorite in dioxane yields the chloro analogs; whereas, reaction of the substituted phenylpyrrole with bromine in chloroform yields the bromine analogs.

| L | M | R | X | Y | mp °C. |
|---|---|---|---|---|---|
| H | H | H | Cl | Cl | 190–190.5 |
| H | 4-Cl | H | Cl | Cl | 214–215 |
| H | 4-Cl | H | Br | Br | 203–204 (dec.) |
| H | H | H | Br | Br | 148.5–149 |
| 3-Cl | 4-Cl | C | Cl | Cl | 219–220 (dec.) |
| H | 4-Br | H | Cl | Cl | 222–223 (dec.) |
| H | H | 4-CF₃ | Cl | Cl | 166–168 |

EXAMPLE 15

Preparation of
4,5-Dichloro-2-(3,4-dichlorophenyl)-1-methyl-pyrrole-3-carbonitrile

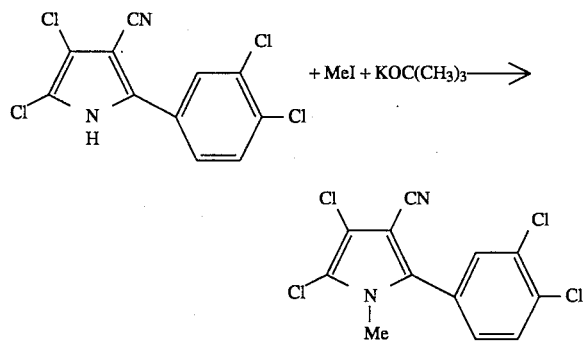

In a 100 mL flask, 2 g of 4,5-dichloro-2-(3,4-dichlorophenyl)pyrrole- 3-carbonitrile in 60 mL dry THF gives a clear brown solution. 1 equivalent of KOtBu is added with stirring, this giving a clear solution after a few minutes. 1 equivalent of MeI is added by syringe and the solution is heated at reflux for 4 hours. It is then left to stir at room temperature overnight. The following day 50 mL of $H_2O$ is added and the mixture extracted with 4× 50 mL $CHCl_3$. The organic phases are combined, dried with $MgSO_4$, and concentrated. The resulting white solid is purified by flash chromatography on silica gel, using 50/50 EtOAc/hexane as an eluent. This gives 1.80 g of a white solid, mp 154°–156° C.

Following the above procedure but substituting the appropriately substituted phenylpyrrole-3-carbonitrile or 3-nitro-2-(substituted)phenylpyrrole for 4,5-dichloro-2-(3,4-dichlorophenyl)pyrrole-3-carbonitrile yields the compounds shown below.

| A | L | M | R | X | Y | mp °C. |
|---|---|---|---|---|---|---|
| $CH_3$ | H | H | 4-Cl | Cl | Cl | 152–153 |
| $C_2H_5OCH_2$ | H | 3-Cl | 4-Cl | Cl | Cl | 128–130 |
| $C_2H_5$ | H | 3-Cl | 4-Cl | Cl | Cl | 137–138 |
| $CH_3$ | H | 3-Cl | 4-Cl | Cl | Cl | 154–156 |
| $CH_3$ | H | H | 4-$CF_3$ | Br | Br | 145–146 |
| $C_6H_5$—$CH_2$ | H | H | 4-$CF_3$ | Br | Br | 145–147 |
| $C_6H_5$—$CH_2$ | H | 3-Cl | 4-Cl | Cl | Cl | 95–96 |
| $CH_2$=CH—$CH_2$ | H | 3-Cl | 4-Cl | Cl | Cl | 69–70 |
| $CH_2$=C—$CH_2Cl$ | H | 3-Cl | 4-Cl | Cl | Cl | |
| CH=C—$CH_2$ | H | 3-Cl | 4-Cl | Cl | Cl | 147–148 |
| $CH_3SCH_2$ | H | 3-Cl | 4-Cl | Cl | Cl | |
| $C(CH_3)_3$ | H | H | 4-$CF_3$ | Cl | Cl | |
| $CH_3$ | H | H | 4-$CF_3$ | Cl | Cl | 99–100 |
| $CH_3SC_2H_5O$ | H | 3-Cl | 4-Cl | Cl | Cl | 74–75 |
| $C_2H_5$—OC—$CH_2$ | H | 3-Cl | 4-Cl | Cl | Cl | 118–120 |
| $C_2H_5$—$OCH_2$ | H | H | 4-$CF_3$ | Cl | Cl | 99–100 |
| $CH_3$ | H | H | 4-$OCH_3$ | Br | Br | 112–115 |
| $CH_3$ | H | H | 4-Cl | Br | Br | 197–201 |
| $C_2H_5OCH_2$ | H | H | 4-$OCF_3$ | Cl | Cl | 46–47 |
| $CH_3$ | H | H | 4-$OCF_3$ | Cl | Cl | 72–73 |

-continued

| A | L | M | R | X | Y | mp °C. |
|---|---|---|---|---|---|---|
| $C_6H_5$—$CH_2$ | H | H | 4-$OCF_3$ | Cl | Cl | oil |
| $C_2H_5OCH_2$ | H | H | 4-Cl | Cl | Cl | — |
| $HOCH_2CH_2$ | H | 3-Cl | 4-Cl | Cl | Cl | 143–145 |
| NC | H | 3-Cl | 4-Cl | Cl | Cl | 251–252 |
| $C_6H_5CH_2OCH_2$ | H | 3-Cl | 4-Cl | Cl | Cl | 88–89 |
| ClO—$CH_2$ | H | 3-Cl | 4-Cl | Cl | Cl | 118–120 |
| IC=C—$CH_2$ | H | 3-Cl | 4-Cl | Cl | Cl | 115–116 |
| $CH_3$ | H | H | 4-Cl | Br | $CF_3$ | 126–129 |
| $C_2H_5OCH_2$ | H | H | 4-Cl | Br | $CF_3$ | 91–92 |
| $C_2H_5$—$OCH_2$ | H | 3-Cl | 4-Cl | Cl | Cl | 118–120 |
| $C_2H_5$—$OCH_2$ | H | H | 4-Cl | Br | Br | 104–105 |
| $C_6H_5$—$CH_2$ | H | H | 4-Cl | Br | Br | 81–82 |
| $CH_3$ | H | H | 4-Cl | Br | Br | 197–201 |
| CN | H | H | 4-$CF_3$ | Cl | Cl | 138–139 |
| $C_2H_5$—$OCH_2$ | H | H | 4-$CF_3$ | Br | $CF_3$ | 104–105 |
| $C_2H_5$—$OCH_2$ | H | H | 4-$CF_3$ | H | $CF_3$ | 76–77 |
| $C_2H_5OCH_2$ | H | 3-Cl | 4-Cl | Br | $CF_3$ | 80–81 |

EXAMPLE 16

Preparation of
1-Benzyl-4,5-dibromo-2-($\alpha,\alpha,\alpha$-trifluoro-p-tolyl)pyrrole-3-carbonitrile

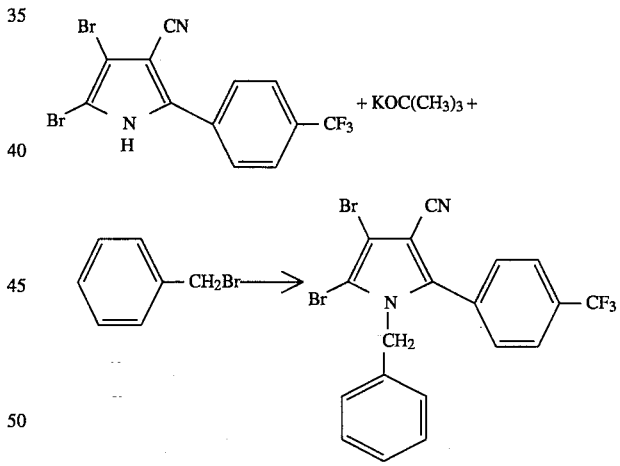

In a 100 mL flask, 1.5 g of 4,5-dibromo-2-($\alpha,\alpha,\alpha$-trifluoro-p-tolyl)pyrrole- 3-carbonitrile is mixed with 50 mL dry THF to give a clear dark solution. 1 eq of KOtBu is added with stirring. After a few minutes the solution clears. Benzyl bromide (0.65 g) is added by syringe. The mixture is heated at reflux overnight. The following day TLC (50/50 EtOAc/hexane) indicates the presence of both starting material and product. The reaction is worked up in the following manner; 50 mL of water is added and the mixture is extracted with 4×50 mL $CHCl_3$. The organic phases are combined and washed with 4×50 mL 10% aq. NaOH. The organic phase is dried with $MgSO_4$ and stripped. This gives a brown solid which is crystallized from EtOAc/hexane, mp 145°–147° C.

EXAMPLE 17

Preparation of
4,5-Dichloro-2-(3,4-dichlorophenyl)-1-(ethoxymethyl)-pyrrole-3-carbonitrile

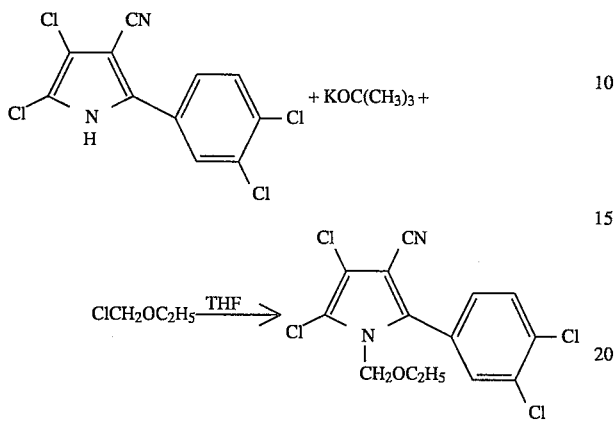

A sample of 4,5-dichloro-2-(3,4-dichlorophenyl)pyrrole-3-carbonitrile (1.0 g, 0.003 mole) is dissolved in 10 mL of dry tetrahydrofuran. To this solution is added potassium t-butoxide (0.37 g, 0.0033 mole) followed by chloromethyl ethyl ether (0.312 g, 0.0033 mole). The mixture is stirred for about 1 hour at room temperature and then poured into a large volume of water precipitating the product. The white solid is collected and dried to give 1.0 g (91%) with mp 128°–130°.

EXAMPLE 18

Preparation of
5-bromo-2-(3,4-dichlorophenyl)pyrrole-3-carbonitrile

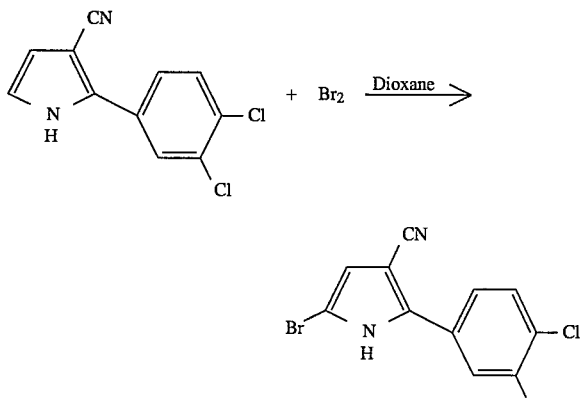

A sample of 2-(3,4-dichlorophenyl)pyrrole-3-carbonitrile (2.0 g, 0.008 mole) is dissolved in 100 mL of dioxane by warming to 40°–50°. Then the solution is cooled to 30° C. and bromine (1.3 g, 0.008 mole) is added. After stirring i hour at room temperature the solution is poured into water and a gray solid (2.2 g, 88%) is collected. The mp is 233°–236° C., decomposition.

In a similiar fashion one can prepare 5-bromo-2-(3,4-dichloro)-3-nitropyrrole starting with 2-(3,4-dichlorophenyl)-3-nitropyrrole.

EXAMPLE 19

Preparation of
5-(p-chlorophenyl)pyrrole-2,4-dicarbonitrile

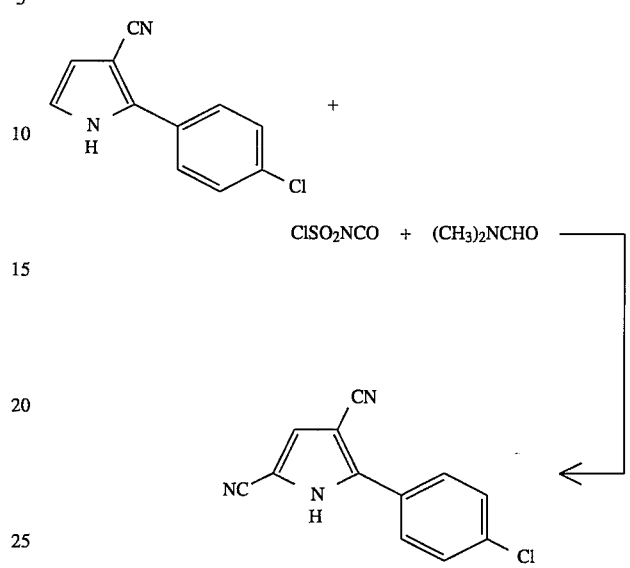

A sample of 2-p-chlorophenyl-3-cyanopyrrole, prepared by the method of Example 4, (3.0 g, 0.015 mole) is dissolved in 50 mL of dry dimethoxyethane. To this solution is added chlorosulfonyl isocyanate (3.39 g, 0.024 mole). The addition is exothermic and some cooling is necessary. After stirring 3 hours at room temperature, dimethylformamide (6–7 mL) is added and the solution is stirred 4 hours more. The solution is then poured into water precipitating a white solid (3.4 g, 100%). A sample (1.0 g) is purified by dissolving in ethyl acetate and then passing the solution through a 60 mL course filter funnel packed with silica gel. The filtrate is concentrated to yield 0.7 g of a white solid with mp 235°–240° C.

Following the procedure of Example 19, the following analogs are prepared:

| R | L | mp |
|---|---|---|
| 3-Cl | 4-Cl | >225° C. |
| H | 4-OCF$_3$ | 185–190° C. |
| H | 4-CF$_3$ | 180–185° C. |

EXAMPLE 20

Preparation of
2-(p-chlorophenyl)-5-(trifluoromethyl)pyrrole-3-carbonitrile 4-(p-chlorophenyl)-2-(trifluoromethyl)-2-oxazolin-5-one (2.5 g; 0.01 mol) is dissolved in nitromethane (50 mL). In a single portion, 2-chloroacrylonitrile (8.0 mL; 0.10 mol) is added to the solution, and the resulting solution is stirred 18 hours at reflux under a nitrogen atmosphere. Cooling the red/brown solution to −5° C. in an ice-acetone bath causes the formation of a precipitate which-is collected by filtration and washed with a small portion of cold nitromethane. The resulting tan solid is recrystallized from hot ethylene dichloride yielding the product as white crystals (1.8 g; 56% theory), mp 238°–241° C. (dec.).

By utilizing the appropriate arylglycine and following the procedure of this Example, the following 2-aryl-5-(trifluoromethyl)pyrrole-3-carbonitrile were prepared:

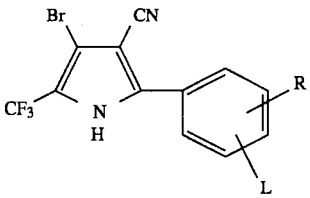

| R | L | mp °C. |
|---|---|---|
| H | H | 215–218 |
| H | 4-CH₃ | 191–193 |
| H | 4-OCH₃ | 168–180 (dec.) |
| 3-Cl | 4-Cl | 245–246 (dec.) |
| H | 4-CF₃ | 218–219 |

EXAMPLE 21

Preparation of
4-Bromo-2-(p-chlorophenyl)-5-(trifluoromethyl)pyrrole-3-carbonitrile Under a nitrogen purge, a suspension or 2-(p-chlorophenyl)-5-(trifluoromethyl)pyrrole-3-carbonitrile( 1.6 g7 0.005 mol) in acetic acid (25 mL) is heated, all the material dissolving to a clear solution at about 60° C. A solution of bromine (0.8 mL; 0.015 mol) in acetic acid (10 mL) is added dropwise over 15 minutes to the refluxing solution. The solution is refluxed 6 hours then allowed to stir 18 hours at room temperature. The HPLC of the reaction mixture shows about 80% conversion to product. The mixture is heated back to reflux and more bromine (0.5 mL; 0.01 mol) in acetic acid (5 mL) is added dropwise. After refluxing another 3 hours, the aliquot shows >95% conversion to product. The reaction is cooled, and solvent removed under reduced pressure on a rotary evaporator to obtain a dark grey solid. Toluene is added to the mixture and removed under reduced pressure, but the odor of acetic acid still remains. The entire material is dissolved in hot toluene (75 mL) to a turbid solution which is treated with DARCO filter and filtered. The light pink solution deposits a white solid upon cooling to ambient. After cooling in the freezer, the solid is collected by filtration, washed with hexanes, and dried on the filter. Further drying in a vacuum oven at 45° C. provides the product (1.2 g; app. 60% theoretical); mp 247°–250° C.

By brominating the appropriate 2-aryl-5-(trifluoromethyl)pyrrole- 3-carbonitrile, according to the above recipe, the following additional examples are prepared:

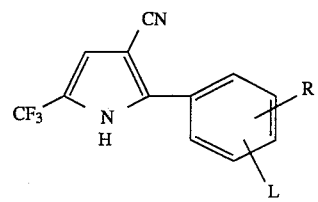

| R | L | mp °C. |
|---|---|---|
| H | H | 235–238 |
| H | 4-CH₃ | 244–245 |
| 3-Cl | 4-Cl | 218–223 |
| H | 4-CF₃ | 225–226 |

EXAMPLE 22

4-Chloro-3-cyano-2-(P-Chlorophenyl)pyrrole

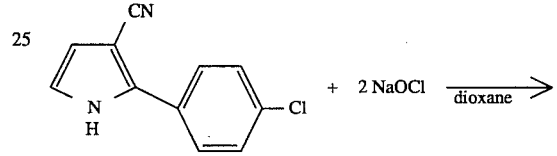

To a magnetically stirred 20° C. solution of 17.87 g (88.2 mmol, 1.00 eq) of 2-(p-chlorophenyl)-3-cyanopyrrole in 800 mL of dioxane is added dropwide 250.15 g (13.13 g real, 176.4 mmol, 2.00 eq) of 5.25 weight % bleach over a period of 30 minutes. After stirring at room temperature for a further 30 minutes, the reaction solution is poured into 2200 mL of water. The resulting mixture is vacuum filtered to remove a small amount of a black solid. The filtrate is acidified to pH 2 with concentrated HCl to produce a brown solid. This solid is vacuum filtered and the collected solids washed with water to give 22.41 g of a brown solid. This solid is treated with 100 mL of 5% aqueous sodium hydroxide to dissolve the bulk of the material while leaving a small amount of undissolved black solid. This black solid, dissolved into 100 mL of ethyl acetate, is washed with 75 mL each of 5% aqueous NaOH, water, and sat. aqueous NaCl. The ethyl acetate layer is dried (MgSO₄), treated with charcoal, filtered, and then rotary evaporated in vacuo to give 1.10 g (5.3% yield) of an orangish brown solid. This solid is recrystallized from at ethyl acetate chloroform mixture to give 0.51 g (2.4% yield) of an off-white solid of 4-chloro-3-cyano-2-(p-chlorophenyl)pyrrole. mp 251°–253.5° C.

EXAMPLE 23

Preparation of
5-bromo-4-chloro-2-(3,4-dichlorophenyl)pyrrole-3-carbonitrile

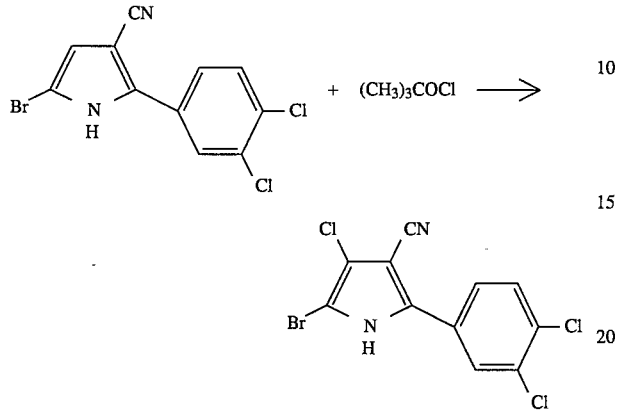

A sample of 5-bromo-2-(3,4-dichlorophenyl)pyrrole-3-carbonitrile (0.158 g, 0.005 mole) is dissolved in tetrahydrofuran (5 mL). An equivalent amount of t-butyl hypochlorite is added and the solution stirred overnight. The solution is poured into water and the precipitate (0.052 g, 30%) is collected. The mp is >275° C.

In a similiar fashion one can prepare 2-bromo- 3-chloro-5-(3,4-dichlorophenyl)-4-nitropyrrole by starting with 2-bromo-5-(3,4-dichlorophenyl)-4-nitropyrrole.

EXAMPLE 24

Preparation of
5-bromo-4-chloro-2-(p-chlorophenyl)-pyrrole-3-carbonitrile

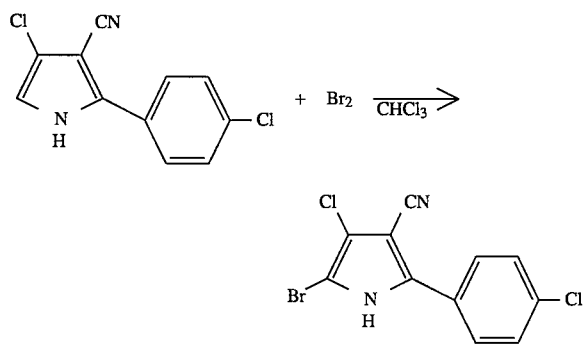

To a magnetically stirred 22° C. solution of 0.17 g (0.67 mmol, 1.00 equivalent) of 4-chloro-2-(p-chlorophenyl)pyrrole- 3-carbonitrile in 100 mL of chloroform is added dropwise over a period of 30 minutes, a solution of 0.20 mL (0.62 g, 3.88 mmol, 5.79 equivalent) of bromine in 5 mL of chloroform. The addition produces no exotherm. After stirring at room temperature for 3¼ hours, the clear red reaction solution is evaporated in vacuo to give 0.28 g of an off-white solid. This solid is slurried with a hexanemethylene chloride mixture to give on vacuum filtration 0.23 g of an off-white fluffy solid. mp 262°–263° C.; dec.

EXAMPLE 25

Preparation of
5-chloro-4-bromo-2-(p-chlorophenyl)-pyrrole-3-carbonitrile

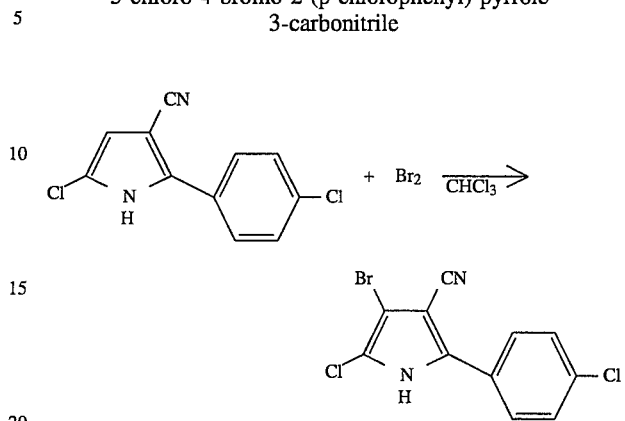

To a magnetically stirred 45° C. solution of 1.00 g (4.22 mmol., 1.00 equivalent) of 5-chloro-2-(p-chlorophenyl)pyrrole- 3-carbonitrile in 300 mL of chloroform is added dropwise over a period of 30 minutes, a solution of 0.40 mL (1.24 g, 7.76 mmol., 1.84 equivalent) of bromine in 25 mL of chloroform. The addition produces no exotherm and towards the end of the addition, a small amount of a solid starts to precipitate. After stirring at room temperature for 19 ½ hours the reaction mixture is evaporated in vacuo to give 1.49 g of an orangish white solid. This solid is slurried with a hexane-methylene chloride mixture to give on vacuum filtration 1.33 g (100% yield) of a fluffy white solid. mp 250°–258° C., dec.

EXAMPLE 26

Preparation of
5-chloro-2-(p-chlorophenyl]pyrrole-3-carbonitrile

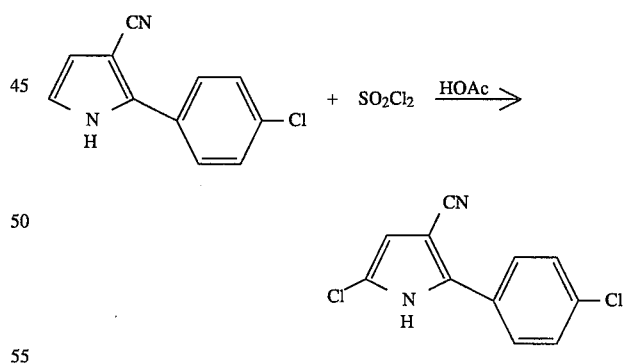

To a 35° C. magnetically stirred solution of 2.40 g (11.8 mmol, 1.00 equivalent) of 2-(p-chlorophenyl)pyrrole- 3-carbonitrile, and 65 mL of glacial acetic acid is added dropwise by syringe 0.75 mL (1.26 g, 9.34 mmol., 0.79 equivalent) of sulfuryl chloride over a period of 5 minutes. Approximately 5 minutes after the completion of the addition, a solid precipitated out of the reaction solution. After stirring at room temperature for 45 minutes, the reaction mixture is filtered and the collected solid is washed well with cold acetic acid to give 2.08 g (74% crude yield) of an off-white solid. This solid is recrystallized from 75 mL of hot acetic

EXAMPLE 27

Preparation of
2-(3,4-dichlorophenyl]-1-methylpyrrole-3-carbonitrile

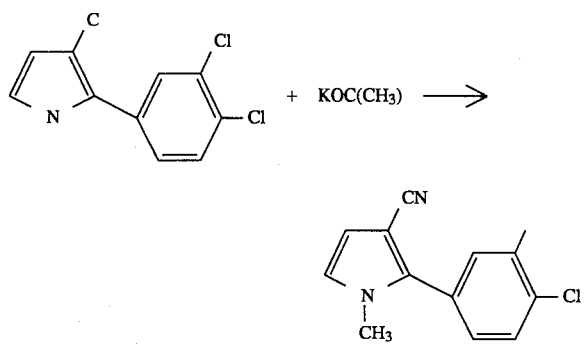

In a 100 mL flask, 2.0 g of 2-(3,4-dichlorophenyl)pyrrole-3-carbonitrile is dissolved in 50 mL of dry THF and 1 equivalent of potassium t-butoxide is added. This gives a slightly cloudy solution. One equivalent of methyl iodide is then added to the mixture by pipette. This leads to a slight lightening of the colour. A drying tube is attached to the flask and it is left to stir at ambient temperature overnight.

The next morning there is a slight light-coloured precipitate in the flask. 50 ml of water is then added and the solution becomes clear before a solid precipitates out of the solution. This solid is filtered out of the solution and compared to the starting material by TLC (25% ethyl acetate/hexane). This indicates a new single spot which is faster moving than the starting material. It is dried in a vacuum oven at 50 deg. C. overnight. The product yield is 1.31 g or 62% yield and has a melting point of 140°–142° C.

EXAMPLE 28

Preparation of
4,5-dichloro-2-(3,4-dichlorophenyl]-1-methylpyrrole-3-carbonitrile

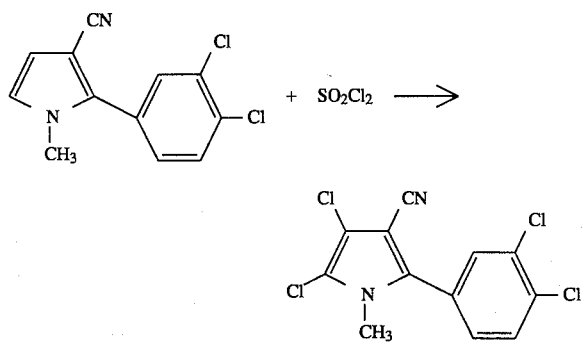

In a 50 mL round bottom flask, 0.8 g of 2-(3,4-dichlorophenyl)- 1-methylpyrrole-3-carbonitrile is mixed with 35 mL of glacial acetic acid. The mixture is warmed slightly with a heat gun to dissolve all of the pyrrole.

To this clear solution is added 2 eq. of sulfuryl chloride by pipette. The solution is left to stir at room temperature for 12 hours.

After 12 hours the solution is poured into 50 mL of water, resulting in a white precipitate. This is filtered out and dried in a vacuum oven at 50° C. for 3 hours.

The resulting solid is identical by TLC, ethyl acetate/hexane), and infrared analysis to the product of Example 9. Product yield is 0.36 (56%).

EXAMPLE 29

Preparation of
4.5-Dichloro-2-(3.4-dichlorophenyl)-1-(2-hydroxyethyl)-pyrrole-2-carbonitrile

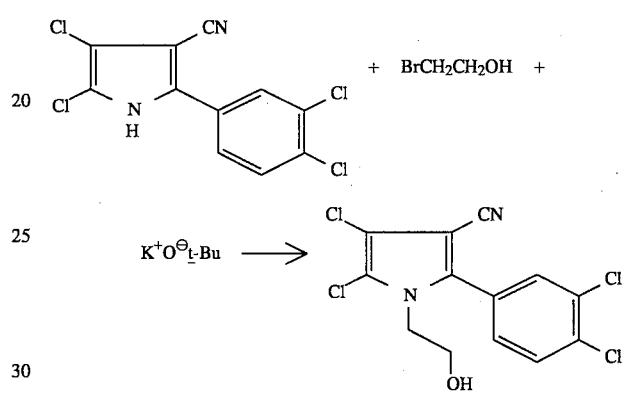

To a stirred mixture of 2.0 g (6.5 mmol) of 4,5-dichloro-2-(3,4-dichlorophenyl) -pyrrole-3-carbonitrile and 0.88 g (7.8 mmol) of potassium tert-butoxide heated at reflux in 50 mL of dioxane is added 0.98 g (7.8 mmol) of bromoethanol. The mixture is stirred at reflux for 12 hours, cooled, diluted with 50 mL of water, and extracted several times with chloroform. The combined chloroform extracts are dried over magnesium sulfate and concentrated in vacuo to leave a solid which, on warming and dissolving in ethyl acetate, deposits on cooling mostly starting pyrrole. Concentration of the mother liquor and recrystallization of the residual solid from 20% ethyl acetate in hexane gives 0.31 g of a white solid, mp 143°–145° C.; IR 5077A.

Anal. Calc'd for $C_{16}H_{23}NO_4$; C, 44.57, H, 2.29; N, 8.00; Cl, 40.57. Found: (Agm 33139): C, 44.77; H, 2.29; N, 8.06; Cl, 40.14.

EXAMPLE 30

Preparation of
4,5-dichloro-2-[3,4-dichlorophenyl)pyrrole-1,3-dicarbonitrile

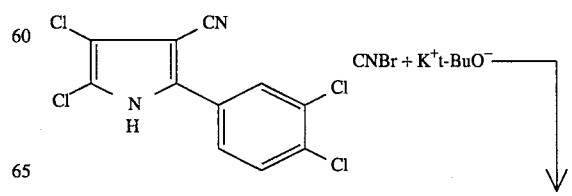

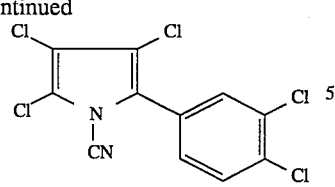

Potassium t-butoxide (617 mg, 55 mmol) is added in portions to a solution of 3-cyano-4,5-dichloro 2-(3,4-dichlorophenyl)pyrrole (1.52 g, 5 mmol ) in anhydrous THF (20 mL). After 30 minutes, a solution of cyanogen bromide (583 mg, 5.5 mmol) in THF (1 mL) is added. The reaction mixture is stored at room temperature overnight. The solvent is removed in a rotary evaporator. The residue is treated with water and extracted witch ethyl acetate. The organic layer is washed with water and saturated sodium chloride and dried (MgSO$_4$). Evaporation and crystallization of the residue from ethyl acetate gives while crystals (1.07 g); mp 250.5°–252.0° C.; IR (nujol) 2255, 2245 cm$^{-1}$ (CN) $^{13}$C NMR (DMSO-d$_6$) 102.7 (N-CN), 113.7 (3-CN); Mass spectrum 331.9 (M+1).

Anal. Calc'd for C$_{12}$H$_3$CP$_4$N$_3$ (330.99); C, 43.54; H, 0.91; N, 12.70; Cl 42.85. Found: C, 4362; H, 0.93, N, 12.63; Cl 41.95.

EXAMPLE 31

Preparation of 4,5-Dichloro-2-(3,4-dichlorophenyl)-1-( 3-iodo-2-propynyl]-pyrrole-3-carbonitrile

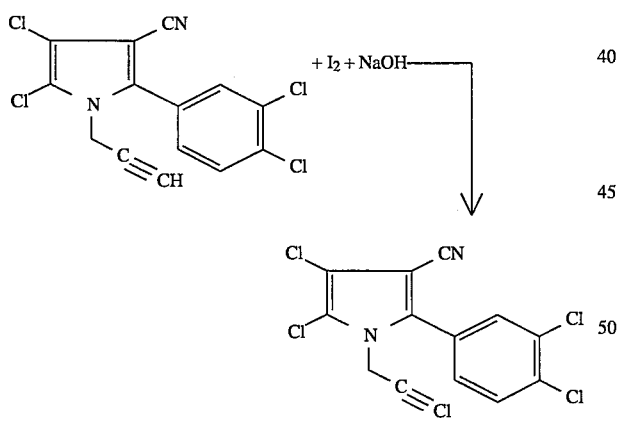

To a stirred mixture of 1.91 g (5.5 mmol) of 4,5-dichloro-2-(3,4-dichlorophenyl)-1-(2-propynyl)-pyrrole- 3-carbonitrile in 500 mL of methanol is added 69 mL of 10% aqueous sodium hydroxide and then 0.70 g (2.7 mmol) of iodine. The mixture is stirred for 12 hours and then acidified and diluted with 200 mL of water. The precipitated solids are collected and recrystallized from methanol to afford 0.51 g while crystals, m.p. 115°–116° C.

This reaction is also applicable to the conversion of any of the formula III, IV, V, VI or VII substituted N-alkynylarylpyrroles of the present invention to N-substituted 3-iodo-2-propynyl arylpyrroles of said invention.

EXAMPLE 12

Preparation of 2-(3,4-dichlorpphenyl)-4,5-diiodopyrrole- 3-carbonitrile

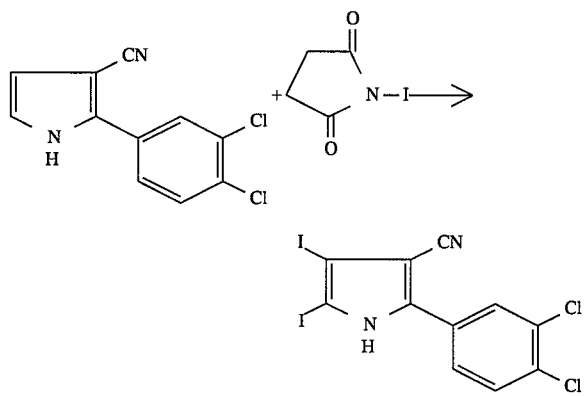

N-iodosuccinimide (5.7 g, 0.0254 mol) is added slowly to a solution of 2-(3,4-dichlorophenyl)pyrrole- 3-carbonitrile (3.0 g, 0.0127 mol) in 100 ml of THF. The reaction is stirred several hours at 25° C. until thin layer chromatography (silica gel; 100:100:1-ether:petrolium ether:acetic acid) shows completion. The mixture is evaporated in vacuo to give a residue containing the pyrrole and succinimide. The crude solid is dissolved in 500 mL of ether and shaken with 5× 400 mL of water to remove the succinimide. The ether is dried over Na$_2$SO$_4$ and evaporated in vacuo to leave 2.0 g (32.3%) of a grey-brown solid with mp >230° (loses purple vapors).

EXAMPLE 33

Preparation of 2-phenyl-1-pyrroline-4-carbonitrile

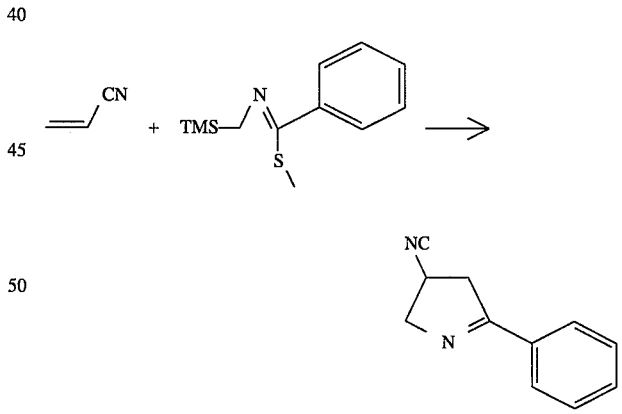

A solution of acrylonitrile (0.65 mL; 0.01 mol) and N-(trimethylsilyl)methyl-S-methyl-benzenethioimidate (2.4 g; 0.01 mol) in THF (100 mL) is cooled to −5° C. in an ice-acetone bath. Under a nitrogen purge, a solution of tetrabutylammonium fluoride (1.0 mL of a 1 N solution in THF) and THF (20 mL) is added dropwise over 30 minutes The solution is stirred another 30 minutes at −5° C., and then allowed to warm slowly to ambient. Stirring is continued another 18 hours, and then solvent is removed under reduced pressure. The residue is partitioned between ether/water and the water layer extracted with fresh ether. The combined organic layer is washed with water, then saturated sodium chloride. The solution is dried over MgSO$_4$, and cooling the filtrate causes precipitation of an off-white solid (1.2 g; 70% theoretical yield) whose spectral characteristics are identical to the material described by Tsuge [J. Org. Chem. 52, 2523 (1987)].

Calcd. for C$_{11}$H$_{10}$N$_2$: C, 77.65; H, 5.88; N, 16.47. Found: C, 77.55; H, 5.83; N, 16.39. mp=95°–97° C.

EXAMPLE 34

Preparation of 2-phenylpyrrole-4-carbonitrile

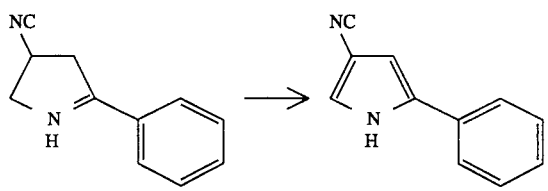

Under a nitrogen purge 2,3-dichloro-5,6-dicyano- 1,4-bonzoquinone (0.23 g; 0.001 mol) and 2-phenyl- 1-pyrroline-4-carbonitrile (0.17 g; 0.001 mol) is dissolved in 1,2-dimethoxyethane (13 mL) to form a clear orange solution. Pyridine (0.08 mL; 0,001 mol) is added in a single portion, causing a slight exotherm (to ca. 28° C.) and an immediate formation of a green/grey precipitate. The suspension is stirred at room temperature for 18 hours during which time much of the solvent evaporates. The brownish semi-solid residue is partitioned between ether and a half-saturated solution of sodium carbonate. The red-brown aqueous layer is extracted twice with ether and the combined ether layer is washed with fresh water, then saturated sodium chloride. After drying with MgSO$_4$, solvent is removed under reduced pressure to obtain a white semi-solid. This material was recrystallized from ethylene dichloride (DARCO treatment) to yield lavender crystals (0.1 g).

The identical product is obtained directly in a single step by condensing α-chloroacrylonitrile and N-(trimethylsilyl-)methyl-S-methyl-benzenethioimidate using tetrabutylammonium fluoride catalysis (analogous to the preparation of 2-phenyl-1-pyrroline-4-carbonitrile described previously).

Calcd. for C$_{11}$H$_8$N$_2$: C, 78.57, H, 4.76; N, 16.67. Found: C, 78.65; H, 4.70; N, 16.43. m.p.=155°–158° C.

EXAMPLE 35

Preparation of 2.4-dibromo-5-phenyl pyrrole-3-carbonitrile

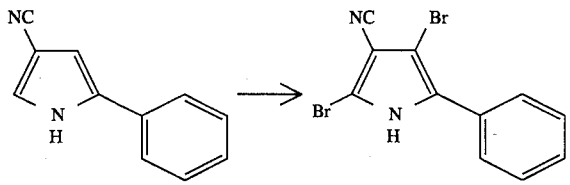

Under a nitrogen purge, a solution of bromine (0.6 mL; 0.012 mol) in CHCl$_3$ (5 mL) is added dropwise over 20 minutes to a stirring solution of 2-phenylpyrrole- 4-carbonitrile (0.84 g; 0.05 mol) in CHCl$_3$ (20 mL). The resulting solution is stirred 18 hours at room temperature, then solvent is removed under reduced pressure to obtain a solid which is recrystallized from C$_2$H$_4$Cl$_2$ (DARCO treatment), yielding the desired final product (0.6 g), m.p. =239°–242° C.

Calcd. for C$_{11}$H$_6$Br$_2$N$_2$: C, 40.49; H, 1.84; Br, 49.08; N, 8.59. Found: C, 39.88; H, 1.87; Br, 48.81; N, 8.48.

By the procedure described in Example 24, 25 and 26, 2,4-dibromo-5-(p-chlorophenyl)pyrrole-3-carbonitrile, m.p. 270°272° C.

EXAMPLE 36

3',4'-Dlchloro-3-[1.3-dioxolan-2-yl)-propiophenone

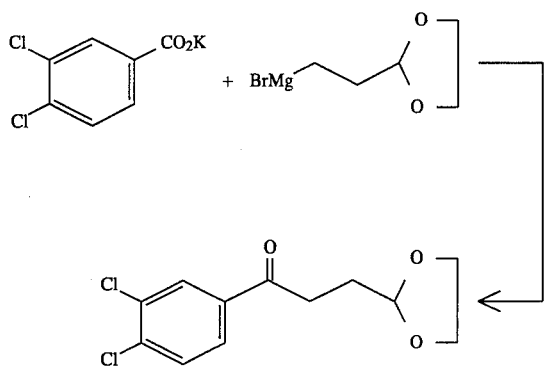

To a rapidly stirring mixture of magnesium turnings (0.64 g, 26 mmol) in 10 mL of tetrahydrofuran at 25° C. in a 100 mL three-neck round bottom flask equipped with a thermometer, a 60 mL addition funnel, and a nitrogen inlet is added dropwise 2-(2-bromoethyl)- 1,3-dioxolane (4.7 g, 26 mmol) in 40 mL of tetrahydrofuran. The rate of addition is adjusted so as to maintain the reaction temperature below 50° C. The reaction is then allowed to stir for i hour at 25° C. 120 mL of tetrahydrofuran is mixed with potassium 3,4-dichlorobenzoate (5.0 g, 22 mmol) under a blanket of nitrogen. The Grignard solution is then quickly decanted away from the unreacted magnesium turnings, and added dropwise to the rapidly stirring potassium benzoate suspension. The reaction is then allowed to stir for 24 hours at 25° C. Fifty mL of diethyl ether and 15 mL of 3N hydrochloric acid are added to the reaction mixture and the layers separated. The organic layer is washed with saturated aqueous sodium bicarbonate until neutral followed by one washing with 10 mL of brine. Drying over sodium sulfate, and rotary evaporation yields a beige semisolid which is chromatographed over silica gel using 3:1 hexane-ethyl acetate as eluent to give the keto-acetal (4.3 g, 60%) as a white solid, m.p. 115°–117° C.

EXAMPLE 37

Preparation of 3-(3,4-dichlorobenzoyl) propionaldehyde

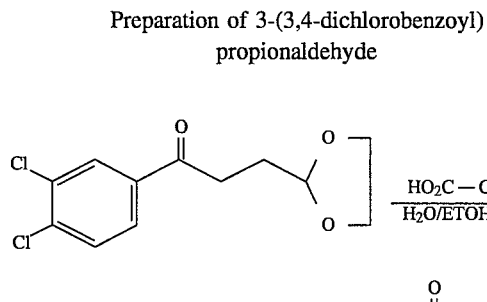

Ten grams (26 mmol) of 3',4'-dichloro-3-(1,3-dioxolan-2-yl)-propiophenone is added to 30 mL of 0.2M oxalic acid (made by dissolving 0.9 g of oxalic acid dihydrate in 30 mL of water) and 5 mL of ethanol. The mixture is refluxed for 1 hour and then allowed to cool. Most of the ethanol is rotary evaporated off and 100 mL of diethyl ether is added along with 20 mL of saturated aqueous sodium bicarbonate. The layers are separated and the organic phase is dried over magnesium sulfate. Rotary evaporation yields a viscous yellow oil which is chromatographed over silica gel using 3:1 hexane-ethyl acetate to give the keto-aldehyde (6.3 g, 75%) as a white solid.

EXAMPLE 38

Preparation of 2-(3.4-dichlorophenyl) pyrrole

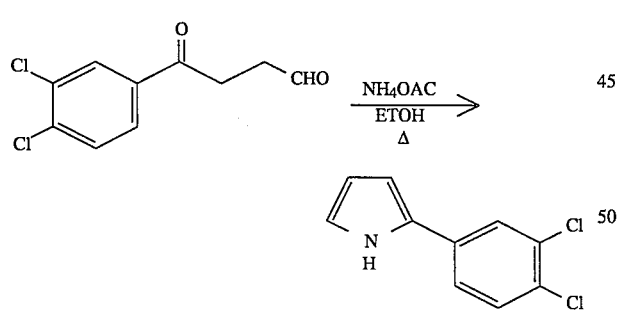

To a suspension of 3-(3,4-dichlorobenzoyl) propionaldehyde (6 g, 26 mmol) in 60 mL of absolute ethanol is added ammonium acetate (4 g, 52 mmol). The reaction is refluxed for 20 minutes and allowed to cool. Most of the ethanol is rotary evaporated and 200 mL of 1:1 dichloromethane-diethyl ether along with 50 mL of water is added. The layers are separated and the organic phase is dried over sodium sulfate. Rotary evaporation yields a dark brown oil which is chromatographed over silica gel using 3:1 hexane-ethyl acetate as eluent to give the pyrrole (4.6 g, 83%) as a light brown solid, m.p. 49°–51° C.

EXAMPLE 39

Preparation of 5-(3,4-dichlorophenyl)pyrrole-2-carboxaldehyde

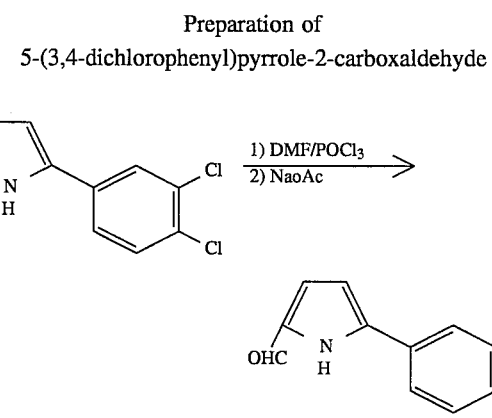

To 10 mL of dimethylformamide stirring under nitrogen in a 50 mL round bottom flask is added phosphorus oxychloride (0.6 mL, 6.5 mmol) dropwise via syringe. The solution, warms and becomes light yellow in color. It is allowed to stir for 20 minutes before the portionwise addition of 2-(3,4-dichlorophenyl)pyrrole (1 g, 4.7 mmol). The beige suspension which results is allowed to stir for 30 minutes before being heated to 50° C. for 40 minutes. A solution of sodium acetate (10 g, 122 mmol) in 15 mL of water is added to the cooled reaction which is then allowed to stir for 20 minutes. A beige precipitate is filtered off from the reaction mixture and air-dried for 20 hours to give the essentially pure aldehyde (1.1 g, 95%), mp >200° C.

EXAMPLE 40

Preparation of 5-(3,4-dichlorophenyl]pyrrole-2-carbonitrile

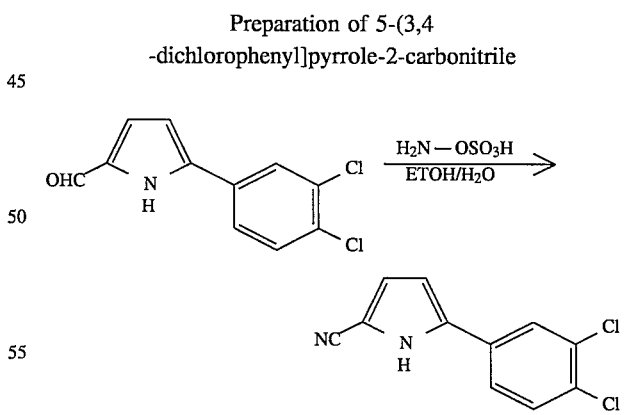

To a suspension of 5-(3,4-dichlorophenyl)pyrrole- 2-carboxaldehyde (1.5 g, 6.2 mmol) in 20 mL of water and 20 mL of ethanol, is added hydroxylamine-O-sulfonic acid (0.7 g, 6.2 mmol). The reaction is refluxed for 1 hour during which time a gray precipitate appears. After being allowed to cool, the reaction is filtered to give essentially pure nitrile (1.5 g, 99%) as a gray solid, m.p. 170°–171° C.

EXAMPLE 41

Preparation of 3,4-dibromo-5-(3,4-dichlorophenyl)pyrrole-2-carbonitrile

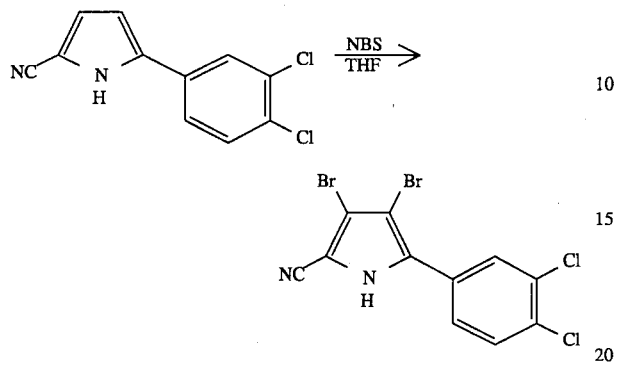

To a solution of 5-(3,4-dichlorophenyl)pyrrole- 2-carbonitrile (0.5 g, 2.1 mmol) in 20 mL of tetrahydrofuran under nitrogen is added portionwise N-bromo-succinimide (0.8 g, 4.2 mmol). The reaction is stirred at 25° C. for 30 minutes before the addition of 10 mL of water and 40 mL of diethyl ether. The layers are separated and the organic layer dried over sodium sulfate. Rotary evaporation is followed by chromatography over silica gel using 3:1 hexane-ethyl acetate as eluent to afford the dibromopyrrole (0.5 g, 60%) as a brown solid, m.p. >250° C.

EXAMPLE 42

Preparation of 4-phenylpyrrole-3-carbonitrile

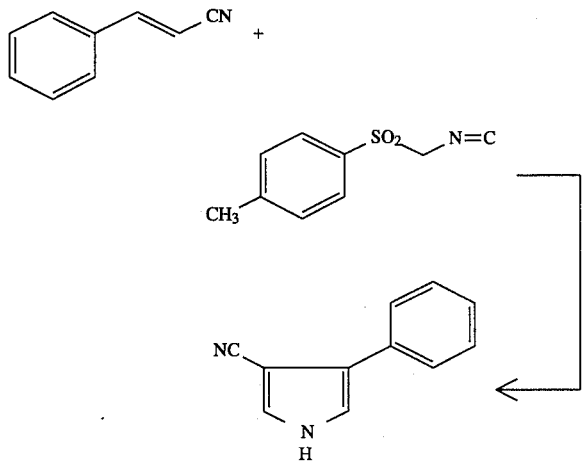

To a mixture of 5.0 g (39 mmol) of cinnamonitrile and 7.6 g (39 mmol) of (p-tolylsulfonyl)methyl isocyanide in 35 mL of DMSO and 65 mL of ether is added over a 20 minute period a suspension of 1.86 g of a 60% oil suspension of sodium hydride (1.11 g; 46 mmol) in 80 mL of ether. The reaction mixture is maintained under nitrogen for an hour and then diluted with ether and water. The ether layer is separated, dried over magnesium sulfate, and concentrated in vacuo. The resulting oil is chromatographed on silica gel using 1:1 chloroform ethyl acetate to give 2.5 g of cream-colored solids. Recrystallization from etherhexane affords 1.15 g, m.p. 123°–125° C.; NMRM86-1077.

Lit.: Tet. Letters 5337 (1972); m.p. 128°–129° C.

EXAMPLE 43

Preparation of 2,5-dichloro-4-phenylpyrrole-3-carbonitrile

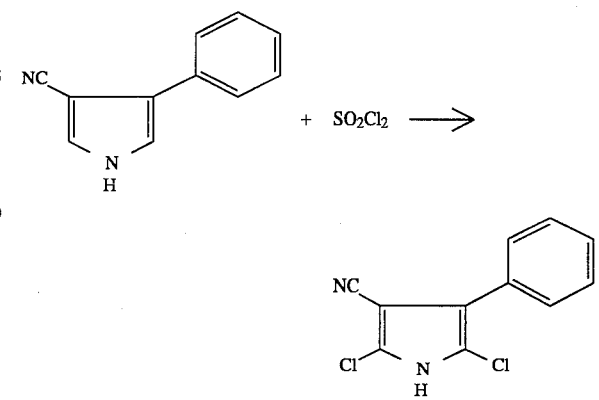

To a stirred mixture of 0.66 g (3.9 mmol) of 4-phenylpyrrole-3-carbonitrile in 20 mL of dry THF cooled to 6° C. with an ice-water bath is added from a syringe 0.66 mL (1.11 g; 8.2 mmol) of sulfuryl chloride over a 4 minute period. The mixture is maintained at 5°–10° C. for an additional 45 minutes and then stirred an additional 30 minutes with the ice bath removed. After the reaction mixture is poured into 80 mL of ethyl acetate and 40 mL of water, the organic phase is separated, washed with water, and dried over sodium sulfate. Filtration through a short column of silica gel, rinsing with ethyl acetate, and concentration of the combined filtrated in vacuo gives 0.95 g of dark solid. Recrystallization from chloroform gives 0.42 g. of off-white crystals, m.p. 195°–196° C. (dec.).

Anal. Calcd. for $C_{11}H_6Cl_2N_2$: C; 55.72; H, 2.55; N, 11.82; Cl, 29.91. Found: C, 55.66; H, 2.65; N, 11.69; Cl, 29.97.

Following the procedures of Examples 33 and 34, the following analogs are prepared. For the synthesis of 2,6-dibromo-4-(p-chlorophenyl)pyrrole-3-carbonitrile, the procedure of Example 33 is followed using bromine in dioxane to replace sulfuryl chloride and tetrahydrofuron.

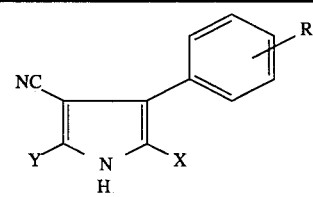

| R | X | Y | m.p. °C. |
|---|---|---|---|
| 4-Cl | Cl | Cl | 237–240 (dec.) |
| 4-CH₃ | Cl | Cl | 103–206 |
| 4-Cl | Br | Br | >245° |

EXAMPLE 44

Ethyl 4-(p-chlorophenyl)-pyrrole-3-carboxylate

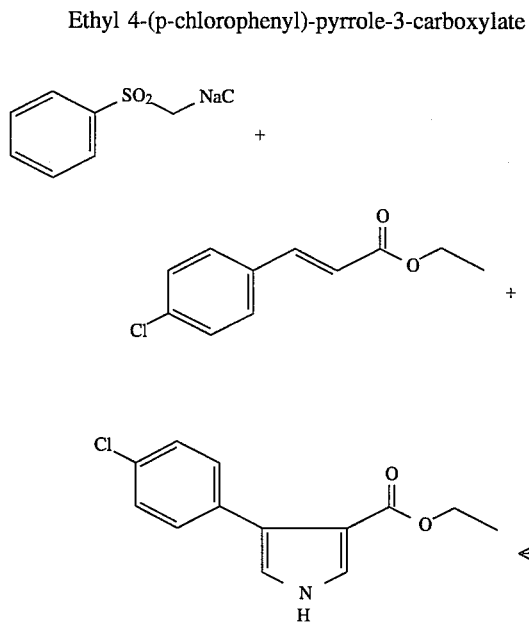

To a mixture of 5.63 g of a 60% sodium hydride/oil suspension in 200 mL of dry ether under nitrogen is added from an additional funnel a mixture of 23.5 g (122 mmol) of ethyl p-chlorocinnamate and 9.4 g (122 mmol) of (p-tolylsulfonyl)methyl isocyanide in solution in 180 mL of ether and 80 mL of dimethylsulfonide. The addition time is about 20 minutes and results in gentle refluxing of the mixture. After another 10 minutes stirring, the mixture is diluted with 100 mL of water. The mixture is extracted four times with ether which is then dried over magnesium sulfate followed by concentrated in vacuo. The resulting solid is recrystallized from ethylene dichlorite to give 7.8 g of crystals, m.p. 137°–138° C.

Anal. Calcd for $C_{13}H_{12}ClNO_2$: C, 62.53; H, 4.81; N, 5.61; Cl, 14.23. Found: C, 61.31, H, 5.12; N, 5.32; Cl, 14.57.

Concentration of the mother liquor for the crystallization leaves additional crude ester which is carried on to the saponification step.

EXAMPLE 45

Preparation of 3-(p-chlorophenyl)-pyrrole

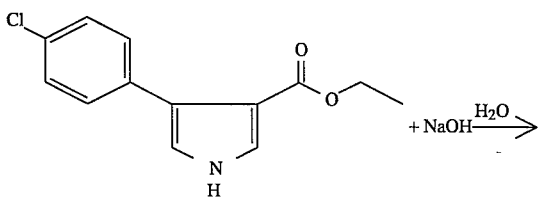

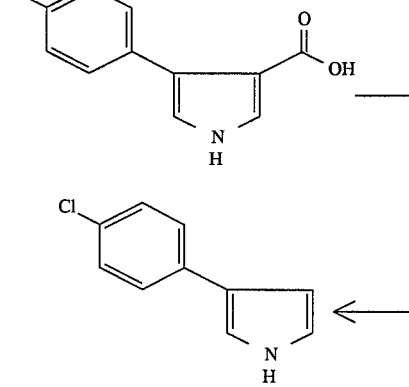

A mixture of 22.0 g of crude ethyl 4-(p-chlorophenyl)-pyrrole- 3-carboxylate from the recrystallization mother liquor and the recrystallized product from the previous step is stirred at reflux with 150 mL of 10% aqueous sodium hydroxide for 2.5 hours. The mixture is cooled, extracted with ether, and acidified to give a precipitate which on collection and drying weighs 11.6 g.

A mixture of 10.5 g of the acid in 100 mL of β-ethanolamine is heated at reflux for three hours. After cooling, the mixture is poured over 400 mL of ice and the resulting mixture is extracted four times with chloroform. The chloroform solution, after drying over magnesium sulfate and treatment with activated charcoal, is concentrated in vacuo to leave a brown solid. Chromatography on silica gel using 1:1 ethyl acetate hexane gives 4.0 g of a white solid, m.p. 117°–118° C.

EXAMPLE 46

Preparation of 3-(p-chlorophenyl)-pyrrole-2-caboxaldehyde

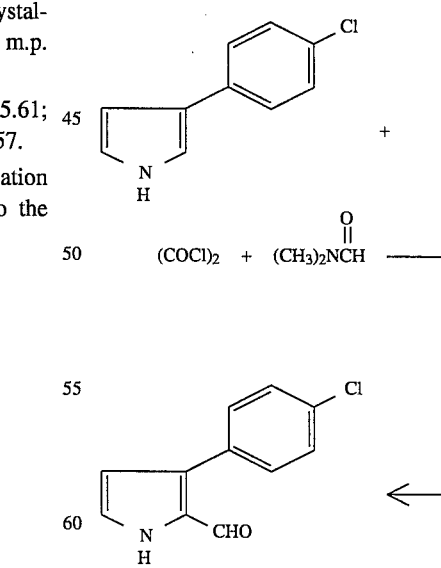

To a mixture of 0.86 g (12 mmol) of dimethylformamide in 10 mL of ethylene dichloride maintained under nitrogen and cooled in an ice bath is added 1.49 g (12 mmol) of oxalyl chloride in 10 mL of ethylene dichloride over a period of 25 minutes. The ice bath is removed, the mixture is stirred an additional 15 minutes and recooled in an ice bath. To this mixture is added 1.5 g (8.5 mmol) of 3-(p-chlorophenyl)-pyrrole in 25 mL of ethylene dichloride over a 20 minute period. The ice bath is removed and after an additional 30 minutes of stirring, the mixture is poured into 50 mL of ice-water and 6 mL of 50% sodium. hydroxide. The resulting mixture is extracted with ether and with chloroform and the combined organic mixture is dried over magnesium sulfate and concentrated in vacuo. Purification of the resulting solid by chromatography on silica gel using 1:1 ethyl acetate hexane gives 0.63 g of off-white solid which is used directly for conversion to 3-(p-chlorophenyl)-pyrrole- 2-carbonitrile.

EXAMPLE 47

Preparation of 3-(p-chlorophenyl)-pyrrole-2-carbonitrile

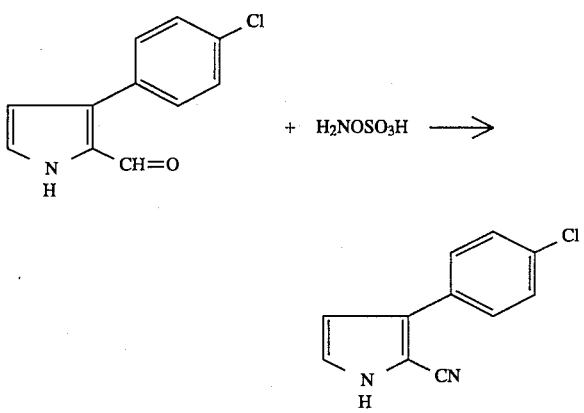

A mixture of 0.63 g (3.1 mmol) of 3-(p-chlorophenyl)-pyrrole- 2-carboxaldehyde in 10 mL of water is stirred and ice-cooled while 0.52 g (4.6 mmol) of hydroxylamine-O-sulfonic acid in 10 mL of water is slowly added. After the addition, the cooling bath is removed and the mixture is heated for 25 minutes. On cooling, the resulting solid is collected and shown, by NMR, to be a mixture of product and starting aldehyde. This mixture is reacted in the same manner with an additional 0.49 g (4.2 mmol) of hydroxylamine-O-sulfonic acid in a total of 30 mL of water. The mixture is heated at 60°–70° C. for 2 hours. The mixture is cooled and the resulting solids are collected and purified by chromatography or silica gel using 1:1 ethyl acetate hexane to give 0.40 g of pink solid, m.p. 114°–115° C.

EXAMPLE 48

Preparation of 4,5-Dibromo-3-(p-chlorophenyl)-pyrrole-2-carbonitrile

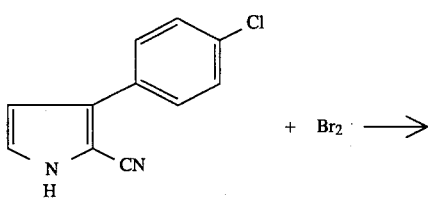

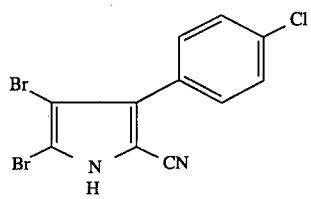

To a mixture 0.40 g (2.0 mmol) of 3-(p-chlorophenylpyrrole)- 2-carbonitrile in 25 mL of chloroform is added 0.63 g (4.0 mmol) of bromine. After 20 minutes, the precipitate which forms is collected and recrystallized from ethyl acetate to give 0.21 g of pink crystals, m.p. >250° C.

Anal. Calcd for $C_{11}H_5Br_2ClN$: C, 36.62; H, 1.39; Br, 44.38t Cl, 9.85; N, 7.77; Found: C, 36.92; H, 1.32; Br, 44.62; Cl, 9.88; N, 7.50

EXAMPLE 49

Preparation of Ethyl 5-bromo-4-(p-chlorophenyl)pyrrole- 3-carboxylate

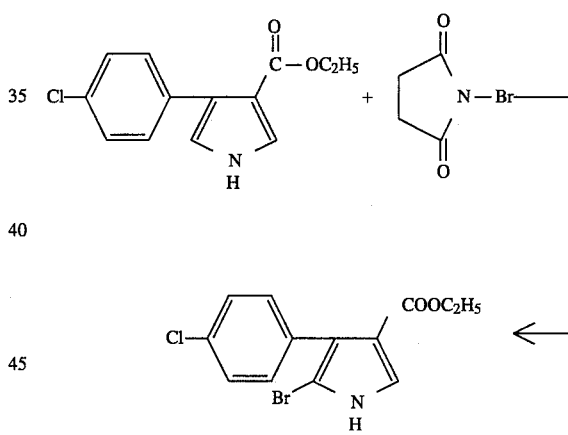

Ethyl 4-(p-chlorophenyl)pyrrole-3-carboxylate (1.6 g., 0.0064 mmol) is dissolved in tetrahydrofuran (40 mL). N-bromosuccinimide (1.14 g., 0.0064 mmol) is added in small portions at 25°–28° C. After the addition is complete, the solution is stirred overnight at room temperature. The solution is concentrated in vacuo and the solid residue partioned between water and ether. The ether layer is separated and dried over magnesium sulfate. Work-up of the ether extract leaves 1.9 g (90%) Of a white solid which is purified by stirring with a mixture of 80/20 hexane/ethyl acetate. The insoluble solid (1.3 g, 62%) is collected and has m.p. 161°–164° C.

Calcd for $C_{13}H_{11}BrClNO_2$: C, 47.50; H, 3.34; N, 4.26; Br, 24.33; Cl, 10.80. Found: C, 47.39; H, 3.38; N, 4.12; Br, 24.29; Cl, 10.77

EXAMPLE 50

Preparation of 5-bromo-4-(p-chlorophenyl)pyrrole-3-carboxylic acid

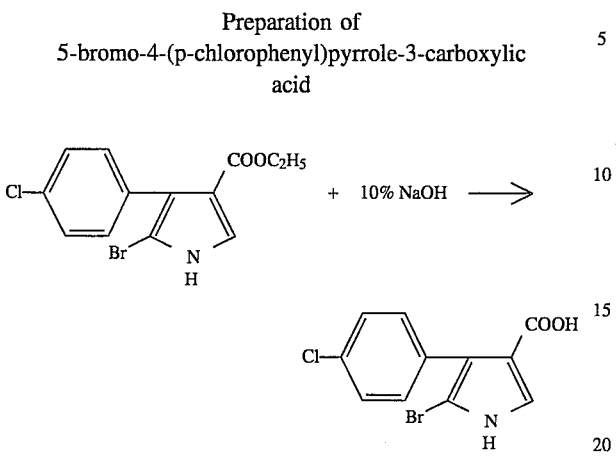

Ethyl 5-bromo-4-(p-chlorophenyl)pyrrole-3carboxylate (15 g., 0.045 mmol) is added to 200 mL of 10% sodium hydroxide and the slurry heated to reflux. After everything appears to dissolve the mixture is refluxed an additional 40 minutes. The mixture is cooled, filtered and the filtrate acidified. The white precipitate (80 g, 58%) is collected and dried. The solid has m.p. >205° C. and an NMR ($d_6$-DMSO) which showed a pyrrole proton at 7.52 (d). The mass spectrum is also consistent for a monobrominated compound.

EXAMPLE 51

Preparation of 2-bromo-3-(p-chlorophenyl)pyrrole

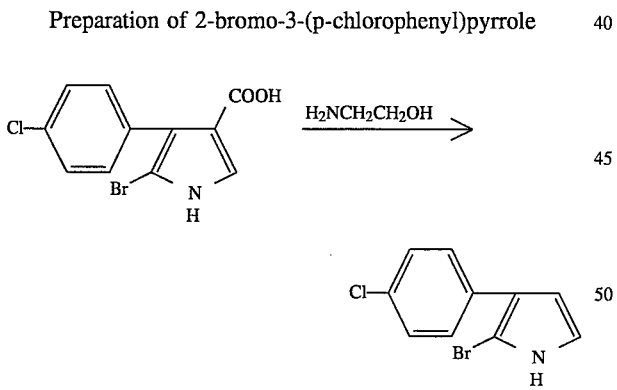

5-bromo-4-(p-chlorophenyl)pyrrole-3-carboxylic acid (8.0 g., 0.026 mmol) is added to aminoethanol (24 mL) and the slurry slowly warmed to 110°–120° C. and held at that temperature for 1 hour. The solution is cooled and poured into water and extracted with ether. The ether extract, by thin layer chromatography (75/25, hexane/ethyl acetate), shows a major fast moving spot and a slower moving minor component. Work-up of the ether leaves a dark solid (4.0 g., 56%) which is 2-bromo- 3-(p-chlorophenyl)pyrrole and is used immediately to prepare 5-bromo-4-(p-chlorophenyl)pyrrole-2-carbonitrile.

EXAMPLE 52

Preparation of 5-bromo-4-(p-chlorophenyl)pyrrole-2-carbonitrile

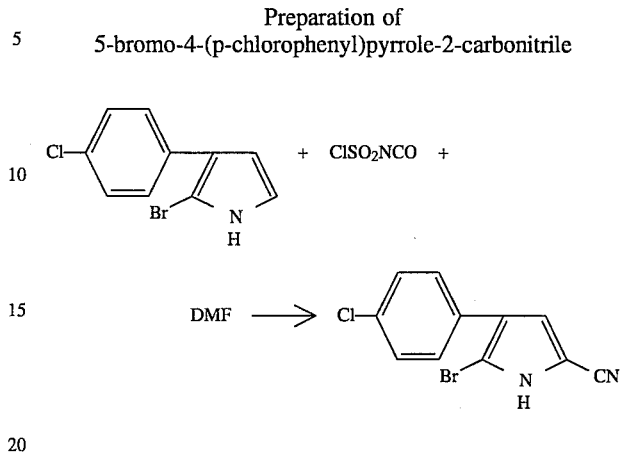

A freshly prepared sample of 2-bromo-3-(p-chlorophenyl)pyrrole (4.0 g., 0,015 mmol) is dissolved in dry dimethoxyethane (25 mL). Then while holding the temperature below 25° C., chlorosulfonyl isocyanate (3.08 g., 0.022 mmol) is added. After stirring overnight, the solution is treated with dimethylformamide (6 mL) and stirred for 3 hours. Finally, the solution is poured into water precipitating a brown solid (3.8 g, 90%). Dry column chromatography (80/20 hexane/ethyl acetate) yields 1.4 g (33%) of white solid with m.p. 202°–204° C.

Calcd for $C_{11}H_6BrClN_2$: C, 46.90; H, 2.13; N, 9.95; Cl, 12.61; Br, 28.39. Found: C, 47.20; H, 2,09; N, 9.80; Cl, 12.36; Br, 27.42.

EXAMPLE 53

Preparation of 3,5-Dibromo-4-(p-chlorophenyl)pyrrole-2-carbonitrile

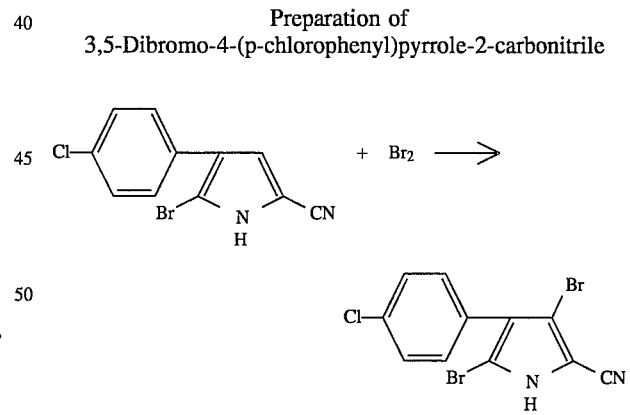

A sample of 5-bromo-4-(p-chlorophenyl)pyrrole- 2-carbonitrile (2.2 g., 0.0078 mol) is dissolved in 30 mL of dry dioxane. The solution is heated with bromine (1.3 g., 0.008 mol) in dioxane (20 mL) and then stirred overnight at room temperature. The reaction mixture is poured into water precipitating a tan solid (2.6 g., 92%). A portion (1.6 g) is purified by flash chromatography using 75/25 hexane/ethyl acetate to give 0.8 g of grey solid with m.p. 191°–194° C.

Calcd for $C_{11}H_5Br_2ClN_2$: C, 36.61; H, 1.38; N, 7.76; Cl, 9.84; Br, 44.3. Found: C, 37,461 H, 1.25; N, 7.41; Cl, 9.53; Br, 42.99.

EXAMPLE 54

Preparation of 3-(3,4-dichlorophenyl)-4-nitropyrrole

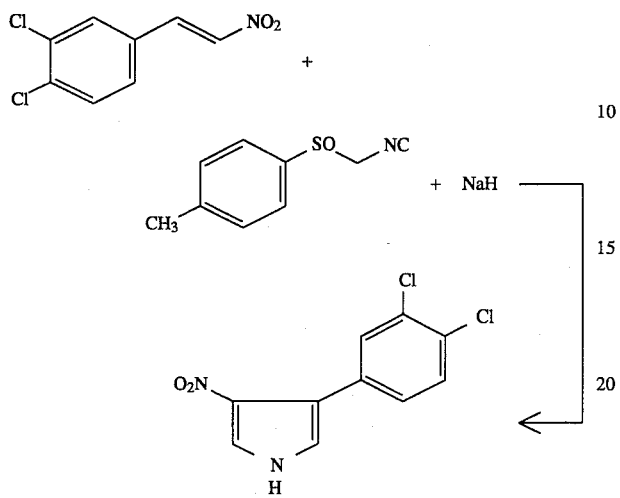

Sodium hydride (2.66 g of a 60% suspension in oil is rinsed with dry ether; 66 mmol) and suspended in 150 mL of dry ether. To this mixture is added over 15 minutes a mixture of 12.0 g (5.5 mmol) of 3,4-dichloro-β-nitrostyrene and 10.8 g (5.5 mmol) of (p-tolylsulfonyl)methyl isocyanide in 50 mL of DMSO and 150 mL of ether. The mixture is stirred for 1.5 hours and then diluted with 150–200 mL of water and additional ether. The ether layer is separated, dried over magnesium sulfate, and concentrated in vacuo. The resulting 10.6 g of crude product is purified by chromatography on silica gel using a 4:1 mixture of chloroform and ethyl acetate. A 7.2 g solid fraction is recrystallized from chloroform-ethyl acetate-hexane to give 3.0 g of yellow solid, m.p. 187°–188° C. (dec.).

Anal. Calcd for $C_{10}H_6Cl_2N_2O_2$: C, 46.72; H, 2.35; N, 10.90. Found: C, 46.96; H, 2.60; N, 9.77

EXAMPLE 55

Preparation of 2,5-Dichloro-3-(3,4-dichlorophenyl)-4-nitropyrrole

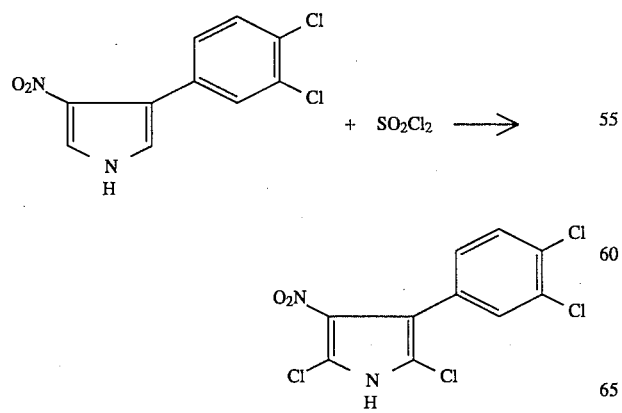

To a mixture of 3-(3,4-dichlorophenyl)-4-nitropyrrole (2.5 g, 9.7 mmol) waned to about 40° C. in 200 mL of chloroform is added over one minute 2.95 g (22 mmol) of sulfuryl chloride. After another hour, the mixture is diluted with 100 mL of saturated sodium bicarbonate solution and 300 mL of ether. The organic layer is separated and dried over magnesium sulfate. Concentration, in vacuo, leaves a brown solid which is chromatographed on silica gel using 4:1 chloroform ethyl acetate. An orange solid fraction is recrystallized from chloroform and then rechromagraphed on silica gel using 4:1 chloroform ethyl acetate to yield 0.36 g of yellow solid, m.p. 193°–194° C.

Also prepared by procedure of Examples 45 and 46 above is 2,5-dichloro-3-nitro-4-phenylpyrrole, m.p. 193°–194° C.(dec.).

EXAMPLE 56

Preparation of 3-Bromo-5-(p-chlorophenyl)-pyrrole-2,4-dicarbonitrile

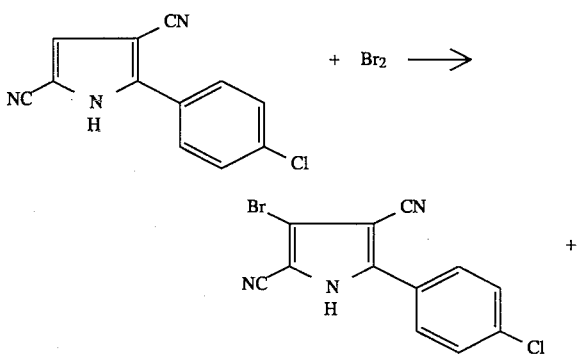

A sample of 5-(p-chlorophenyl)pyrrole-2,4-dicarbonitrile (1.0 g, 0.004 mole) is dissolved in 20 mL of dioxane and a solution of bromine (0.8 g, 0.005 mole) in dioxane (10 mL) is then added thereto. The solution is stirred several hours at room temperature and then poured into water precipitating a white solid (1.2 g, 100%). The solid has a m.p. >225° C. and a mass spectrum of a sample gives a pattern consistent with the desired structure.

Following the procedure set forth above in Example 48, the following additional compounds are prepared:

| R | L | m.p. |
|---|---|---|
| 3-Cl | 4-Cl | >250° C. |
| H | 4-OCF$_3$ | 218–223° C. |
| H | 4-CF$_3$ | 239–241° C. |

EXAMPLE 57

Preparation of bromofumaronitrile

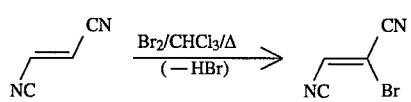

Under a nitrogen purge, fumaronitrile (15.6 g; 0.2 mol) in CHCl₃ (150 mL) is heated to reflux, resulting in a clear solution. A solution of bromine (5.3 mL; 0.2 mol) in CHCl₃ (25 mL) is added dropwise over 30 minutes, resulting in a slow decolorization and acidic (pH test paper) fumes being released. The solution is refluxed another 90 minutes, during which time most of the color has been discharged. The solution is cooled and solvent is removed under reduced pressure, leaving an amber oil (weight approximately theoretical for bromofumaronitrile). The oil is subjected to bulb-to-bulb distillation (0.2 mm Hg), maintaining the temperature below 120° C. (above that point, a rapid decomposition of material occurs). A semi-solid is obtained which slowly forms a waxy, amber solid, m.p. –43°–47° C.

Calcd for $C_4HBrN$: C, 30.57; H, 0.64; N, 17.83. Found: C, 29.13; H, 0.75; N, 16.94.

EXAMPLE 58

Preparation of 2-phenyl-pyrrole-3,4-dicarbonitrile

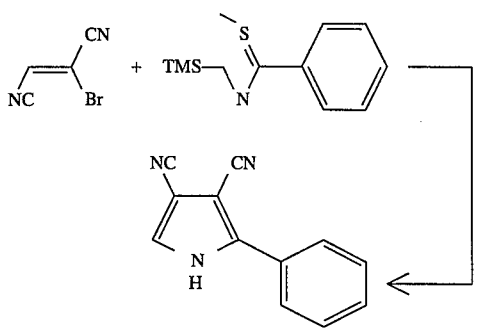

Under a nitrogen purge, a solution of bromofumaronitrile (4.7 g; 0.03 mol) and N-(trimethylsilyl) methyl-S-methyl-benzene-thioimidate (7.1 g; 0.03 mol) in hexamethylphosphoramide (HMPA) (35 mL) is stirred at room temperature. In a single portion, water (1.6 mL); 0.09 mol) is added, washed in with HMPA (10 mL). The solution almost immediately begins to exotherm, the temperature rapidly reaching 100° C. before subsiding. The resulting dark red solution is allowed to stir at ambient temperature 20 hours. Pouring the reaction mixture onto an ice/water mixture results in a gummy material which slowly yields a discreet beige solid. This material is collected by filtration and washed with cold water and dried on the filter. After further drying (vacuum oven; 60° C.), the material is twice recrystallized from $C_2H_4Cl_2$ (DARCO treatment) to yield a white powder.

Calcd for $C_{12}H_7N_3$: C, 74.61; H, 3.63; N, 21.76. Found: C, 74.45; H, 3.84; N, 21.61. m.p. =197°–200° C.

EXAMPLE 59

Preparation of 2-bromo-5-phenylpyrrole-3,4-dicarbonitrile

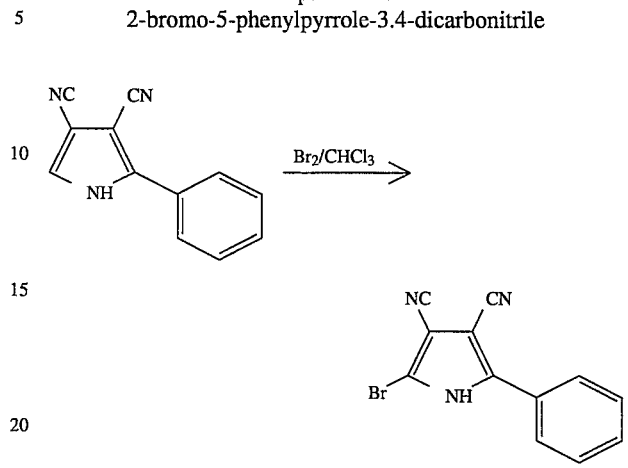

Under a nitrogen purge, 2-phenyl-pyrrole-3,4-dicarbonitrile (1.4 g; 0.0075 mol) is added to CHCl₃ (35 mL), much of the solid dissolving. A solution of bromine ( 0.4 mL; 0.008 mol) in CHCl₃ (5 mL) is added dropwise over 20 minutes. Initially the color is discharged rapidly, but as a new, gummy solid begins to precipitate, the color remains. After stirring 30 minutes at ambient, the mixture is brought to reflux, resulting in a much more discreet solid. After refluxing 90 minutes, the reaction mixture is cooled and an aliquot is removed and analyzed (HPLC), showing ca. 60% starting material still remaining. In a single portion fresh bromine (0.2 mL; 0.004 mol) is added, and refluxing continued another 45 minutes whereupon an aliquot shows 10% starting material remaining. Another fresh portion of bromine (0.2 mL; 0.004 mol) is added to the refluxing suspension and refluxing is continued another 30 minutes. The suspension is cooled and stirred 18 hours at room temperature. Solvent removed under reduced pressure to yield a greenish solid which is extracted with hot CHCl₃, leaving behind a dark residue. The extract is treated with DARCO and filtered hot. The Clear yellow filtrate quickly began to deposit a white precipitate. After cooling to –10° C., the white solid is collected by filtration.

Calcd for $C_{12}H_6BrN_3$: C, 52.94; H, 2.21; N, 15.44; Br, 29.41. Found: C, 51.64; H, 2.35; N, 14.91; Br, 28.69. m.p. =225°–258° C.

EXAMPLE 60

Preparation of 2-(3,4-Dichlorophenyl-5-nitropyrrole-3-carbonitrile

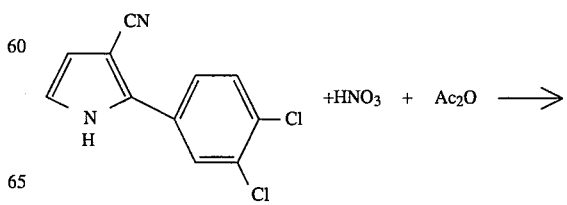

-continued

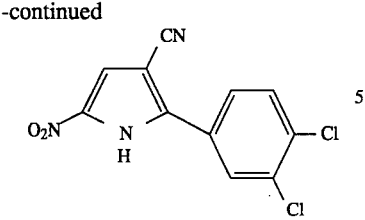

2-(3,4-Dichlorophenyl)pyrrole-3-carbonitrile (3.0 g, 0.013 mole) is added to acetic anhydride (50 mL) and 90% nitric acid (0.6 ml) with very little exotherm. The mixture is slowly warmed to 30° and is then held at 30°–33° until everything goes into solution. Gradually a new solid precipitates. The mixture is stirred for 2 to 3 hours at room temperature and then poured into water and ice to decompose the acetic anhydride. After stirring 1 hour the mixture is filtered and the solid (2.9 g, 82%) collected and dried. A portion (1.5 g) is purified by column chromatography on silica gel using 75/25 hexane/ethyl acetate for elution to give 0.7 g of yellow solid with m.p. 228°–231°.

Calcd for $C_{11}H_5Cl_2N_3O_2$: C, 46.80; H, 1.77; N, 14.89; Cl, 25.17 Found: C, 46.50; N, 1.96; N, 14.27; Cl, 24.30.

By the same procedure, starting with 2-(p-chlorophenyl)pyrrole- 3-carbonitrile, 2-(p-chlorophenyl)- 5-nitropyrrole-3-carbonitrile is obtained, m.p. 201°–206° C. Also, 2-(p-trifluoromethylphenyl)pyrrole-3-carbonitrile gives 2-(p-trifluoromethylphenyl)-5-nitropyrrole- 3-carbonitrile by the above procedure. This compound has a melting point of 164°–165.5° C.

EXAMPLE 61

Preparation of
4-Bromo-2-(3,4-dichlorophenyl)-5-nitropyrrole-
3-carbonitrile

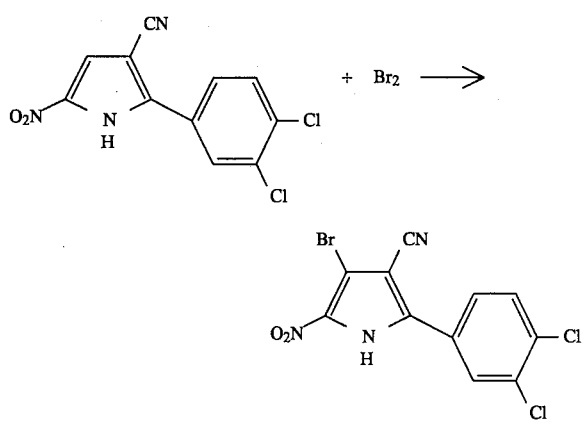

2-(3,4-Dichlorophenyl)-5-nitropyrrole-3-carbonitrile (0.5 g, 0.0017 mol) is dissolved in dry dioxane (10 mL). To this solution is added bromine (0.28 g, 0.0017 mole) in dioxane. After stirring overnight, the solution is poured into water precipitating a tan solid (0.54 g, 88%). Recrystallization from acetonitrile (5 mL) gives 0.26 g of tan solid with m.p. 195°–200° C.

Calcd for $C_{11}H_4BrCl_2N_3O_2$: C, 36.57; H, 1.10; N, 11.63; Br, 22.13; Cl, 19.67. Found: C, 36.46; H, 1.29; N, 11.50; Br, 21.63; Cl, 19.28.

Following the above procedure of Example 53, but starting with 2(p-chlorophenyl)-5-nitropyrrole-3-carbonitrile gives 4-bromo-2-(p-chlorophenyl)-5-nitro-pyrrole- 3-carbonitrile, m.p. 180°–185° C.

EXAMPLE 62

5-(3,4-Dichlorophenyl)-4-nitropyrrole-2-carbonitrile

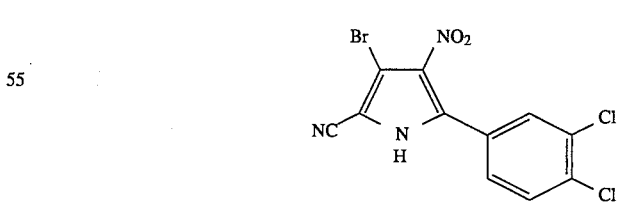

To a suspension of 5-(3,4-dichlorophenyl)pyrrole- 2-carbonitrile (1.2 g, 5.1 mmol) in 25 mL of acetic anhydride at 30° under nitrogen, is added dropwise 90% nitric acid (0.3 mL, 5.1 mmol). The reaction exotherms to 45° C. and becomes a green solution. After being allowed to stir for 2 hours the reaction is poured into 50 mL of water and stirred vigorously for 5 minutes. The beige precipitate which results is filtered off and dissolved in a minimum amount of acetone. Chromatography over silica gel using 3:1 hexane-ethyl acetate affords the nitropyrrole (1.2 g, 84%) as an off-white solid, m.p. >200° C.

EXAMPLE 63

3-Bromo-5-(3,4-dichlorophenyl)-4-nitropyrrole-2-
carbonitrile

To a suspension of 5-(3,4-dichlorophenyl)-4-nitropyrrole-2-carbonitrile (0.6 g, 2.1 mmol) in 10 mL of dioxane at 25° C., under nitrogen, is added dropwise a solution of bromine (0.3 g, 2.1 mmol) in 5 mL of dioxane. The reaction is allowed to stir overnight. Addition of 50 mL of water causes precipitation of a yellow solid which is collected and vacuum oven dried (50 mm Hg, 45° C.) to afford the brominated pyrrole (0.7 g, 90%) as a light yellow solid, m.p. >200° C.

EXAMPLE 64

4-(p-chlorophenyl)-2-(trifluoromethyl-2-oxazolin-5-one

In a single portion, trifluoroacetic anhydride, (1.7 mL; 0.012 mol) is added to powdered 2-(p-chlorophenyl)glycine (11.4 g; 0.06 mol), causing an immediate exotherm to about 40° C., a yellow color forming on the surface of the solid. As the mixture is slowly heated to 70° C., more of the solid dissolves to an orange/amber oil. All the solid dissolved in approximately 2 hours, and heating is continued another hour. Solvent is removed under reduced pressure on a rotary evaporator. Toluene is twice added and removed under reduced pressure, but the odor of trifluoroacetic acid is still evident. This yellow semi-solid (yield theoretical; purity >90% by HPLC) is the above-identified compound and is used in the next step without further purification.

EXAMPLE 65

Preparation of 2-(4-chlorophenyl)-5-trifluoromethylpyrrole-3,4-dicarbonitrile

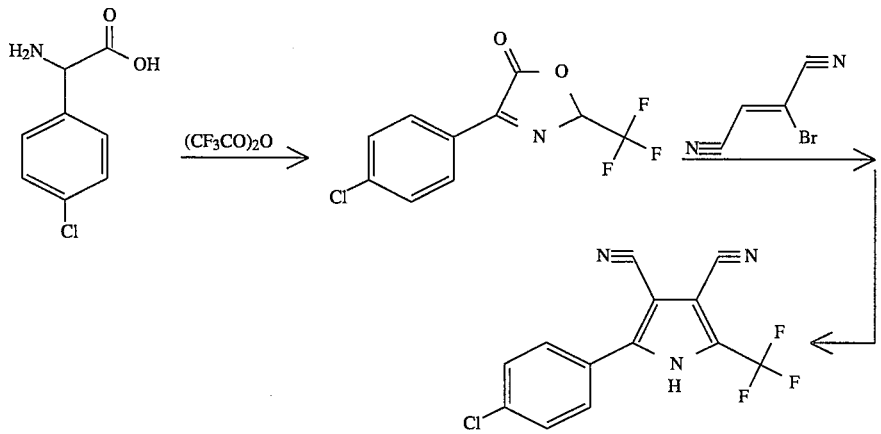

Trifluoroacetic anhydride (3.1 mL; 0.022 mol) is added in a single portion to (4-chlorophenyl)glycine (2.0 g; 0.011 mol), causing an immediate yellow color and some refluxing. The mixture is slowly heated to reflux, causing all the material to dissolve to a yellow/orange solution which is heated 2 hours further. The reaction mixture is cooled, and solvent removed under reduced pressure. Toluene, is twice added and removed under reduced pressure to yield a very thick oil ($V_{CO}$=1800cm$^{31\ 1}$). This residue is dissolved (some insolubles) in $CH_3NO_2$ (40 mL). and bromofumaronitrile (2.7 g; 0.018 mol) is added in a single portion. The resulting solution is heated at reflux 18 hours, yielding a dark red solution. Solvent is removed under $CH_2Cl_2$), some insolubles being removed by filtration reduced pressure and the dark residue is dissolved in The material is factionated via dry column chromatography (silica gel; 3% 2-PrOH in $CH_2Cl_2$), and appropriate fractions are taken. Evaporation of one fraction yields the desired compound as a yellow solid which is recrystallized from $CH_3CN$ (DARCO treatment) to yield a pale yellow solid (0.2 g). m.p.=238°–241° C. (some dec).

What is claimed is:

1. A method for protecting a warm-blooded animal from infestation by helminths, acarids and arthropod endo- and ectoparasites which comprises administering or applying to said animal an anthelmintically, acaricidally or parasticidally effective amount of a substituted arylpyrrole compound having the structure

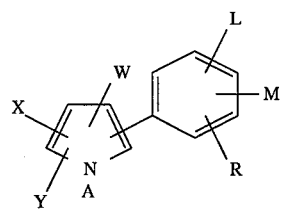

wherein

X is H, F, Cl, Br, I or $CF_3$;

Y is H, F, Cl, Br, I, $CF_3$ or CN;

W is CN or $NO_2$;

A is H;

$C_1$–$C_4$ alkyl optionally substituted with substituents selected from the group consisting of
one to three halogen atoms
one hydroxy,
one $C_1$–$C_4$ alkoxy,
one $C_1$–$C_4$ alkylthio,
one phenyl optionally substituted with
$C_1$–$C_3$ alkyl,
$C_1$–$C_3$ alkoxy, or
one to three halogen atoms,
one phenoxy optionally substituted with one to three halogen atoms, and
one benzyloxy optionally substituted with one halogen substituent;

$C_1$–$C_4$ carbalkxoymethyl;

$C_3$–$C_4$ alkenyl optionally substituted with one to three halogen atoms;

cyano;

$C_3$–$C_4$ alkynyl optionally substituted with one halogen atom;

di-($C_1$–$C_4$ alkyl) aminocarbonyl; or $C_4$–$C_6$ cycloalkylaminocarbonyl;

L is H, F, Cl or Br: M and R are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$, $R_1CF_2Z$, $R_2CO$ or $MR_3R_4$, and when M and R are on adjacent positions and taken with the carbon atoms to which they are attached they may form a ring in which MR represents the structure:

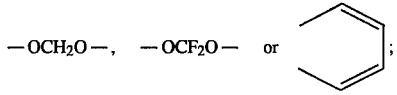

Z is $S(O)_n$ or O;

$R_1$ is H, F, $CHF_2$, CHFCl, or $CF_3$;

$R_2$ is $C_1$–$C_3$ alkyl, $C_1$–$C_3$ alkoxy, $NR_3R_4$;

$R_3$ is H or $C_1$–$C_3$ alkyl;

$R_4$ is H, $C_1$–$C_3$ alkyl or $R_5CO$;

$R_5$ is H or $C_1$–$C_3$ alkyl;

and n is an integer of 0, 1 or 2.

2. The method according to claim I for controlling acarids and arthropod ectoparasitic insect infestations on a meat producing or companion animal by topically applying a composition containing the compound to the skin, hair and hide of said animal.

3. The method according to claim 2, wherein the composition is applied as an aqueous spray containing about 0.1 ppm to 500 ppm of the compound.

4. The method according to claim 2, wherein the composition is applied as a pour-on containing about 0.5% to 30% by weight of the compound, about 0.5% to 30% by weight of a spreading oil, about 30% to 60% by weight of a diluent selected from the group consisting of mono alcohols, polyhydric alcohols, vegetable oils, spreading oils, aliphatic hydrocarbons, aromatic hydrocarbons, lower alkyl ketones, esters and fatty acids or mixtures thereof and up to about 20% by weight of an oil wherein the oil is a vegetable or mineral oil.

5. The method according to claim 2, wherein the meat-producing animal is selected from the group consisting of swine, cattle, sheep, horses, goats and poultry and the companion animal is a dog or cat.

6. The method according to claim 1 for reducing helminth infestations in a meat-producing or companion animal by orally administering thereto an agronomically acceptable carrier containing about 0.1 ppm to 500 ppm of the compound selected from the group consisting of 3-bromo-5-p-chlorophenyl)pyrrole-2,4-dicarbonitrile; 4-bromo- 2-(p-chlorophenyl)pyrrole-2,4-dicarbonitrile; 4-bromo- 2-(p-chlorophenyl)-1-(ethoxymethyl)-5-(trifluoro methyl)pyrrole-3-carbonitrile; 4-bromo-2-(3,4-dichloro phenyl)-1-(ethoxymethyl)-5-(trifluoromethyl)pyrrole-3-carbonitrile; 4-bromo-2-(3,4-dichlorophenyl)-1-ethoxy methyl-5-(trifluoromethyl)pyrrole-3-carbonitrile; 4,5-dichloro-1-(hydroxymethyl)-2-($\alpha,\alpha,\alpha$-trifluoro-p-tolyl)pyrrole- 3-carbonitrile acetate ester; and 3-nitro- 2-phenyl-4,5-bis(trifluoromethyl)pyrrole.

7. The method according to claim 6, wherein the meat-producing animal is selected from the group consisting of swine, cattle, sheep, horses, goats and poultry and the companion animal is a dog or cat.

* * * * *

UNITED STATES PATENT AND TRADEMARK OFFICE
CERTIFICATE OF CORRECTION

PATENT NO. : 5,455,263
DATED : October 3, 1995
INVENTOR(S) : Mary E. Doscher

It is certified that error appears in the above-indentified patent and that said Letters Patent is hereby corrected as shown below:

Claim 1, column 57, line 2 should read:

"nitro, $CF_3$, $R_1CF_2Z$, $R_2CO$ or $NR_3R_4$, and when M and"

Signed and Sealed this

Nineteenth Day of December, 1995

BRUCE LEHMAN

Attest:

Attesting Officer

Commissioner of Patents and Trademarks